US008945067B2

(12) United States Patent
McLoughlin et al.

(10) Patent No.: US 8,945,067 B2
(45) Date of Patent: Feb. 3, 2015

(54) SYSTEMS FOR ADMINISTERING MEDICATION

(75) Inventors: Martin John McLoughlin, Hemel Hempstead (GB); Alex Lee, New York, NY (US); Dan Formosa, Piermont, NY (US); Steven Vordenberg, Amherst, NH (US); Joern Vicari, Brooklyn, NY (US); Eric Freitag, New York, NY (US); Boris Kontorvich, Brooklyn, NY (US)

(73) Assignee: UCB Pharma, S.A., Brussels (BE)

( * ) Notice: Subject to any disclaimer, the term of this patent is extended or adjusted under 35 U.S.C. 154(b) by 43 days.

(21) Appl. No.: 12/506,059

(22) Filed: Jul. 20, 2009

(65) Prior Publication Data
US 2010/0016795 A1 Jan. 21, 2010

Related U.S. Application Data

(60) Provisional application No. 61/135,262, filed on Jul. 18, 2008, provisional application No. 61/192,551, filed on Sep. 18, 2008.

(51) Int. Cl.
*A61M 5/32* (2006.01)
*A61M 5/31* (2006.01)
*A61M 5/00* (2006.01)
*A61M 5/20* (2006.01)

(52) U.S. Cl.
CPC .......... *A61M 5/3202* (2013.01); *A61M 5/3137* (2013.01); *A61M 5/2033* (2013.01); *A61M 5/3134* (2013.01); *A61M 5/3204* (2013.01); *A61M 2005/3215* (2013.01)

USPC ............ 604/192; 604/198; 604/263; 604/187

(58) Field of Classification Search
CPC  A61M 5/3204; A61M 5/3202; A61M 5/3137
USPC .......................................... 604/198, 192, 134
See application file for complete search history.

(56) References Cited

U.S. PATENT DOCUMENTS

| | | |
|---|---|---|
| 2,799,272 A | 7/1957 | Peach |
| 4,248,246 A | 2/1981 | Ikeda |
| 4,365,626 A | 12/1982 | House |
| 4,474,734 A | 10/1984 | Cooper |
| 4,490,142 A | 12/1984 | Silvern |
| 4,636,201 A | 1/1987 | Ambrose et al. |
| 4,728,320 A | 3/1988 | Chen |
| 4,767,413 A | 8/1988 | Haber et al. |
| 4,863,433 A | 9/1989 | Payne et al. |
| 4,892,525 A | 1/1990 | Hermann, Jr. et al. |
| 4,919,657 A | 4/1990 | Haber et al. |

(Continued)

FOREIGN PATENT DOCUMENTS

| | | |
|---|---|---|
| DE | 60112770 | 3/2006 |
| EP | 1 453 561 | 9/2004 |

(Continued)

*Primary Examiner* — Quynh-Nhu H Vu
*Assistant Examiner* — Jenna Zhang
(74) *Attorney, Agent, or Firm* — Ropes & Gray LLP

(57) ABSTRACT

The autoinjector systems disclosed herein provide in part devices for allowing patients with reduced joint strength to more easily administer medicine. Certain exemplary syringe embodiments include a housing, a syringe assembly slidably mounted on the housing, and a needle cap releasably engaged to the housing, where the cap includes a protruding pocket for receiving a needle cap remover.

14 Claims, 28 Drawing Sheets

(56) References Cited

U.S. PATENT DOCUMENTS

| | | |
|---|---|---|
| 4,964,866 A | 10/1990 | Szwarc |
| 4,985,020 A | 1/1991 | Kasuya |
| 4,986,818 A | 1/1991 | Imbert et al. |
| 5,013,299 A | 5/1991 | Clark |
| 5,067,944 A | 11/1991 | Nichols |
| 5,098,400 A | 3/1992 | Crouse et al. |
| 5,108,378 A | 4/1992 | Firth et al. |
| 5,135,514 A | 8/1992 | Kimber |
| 5,250,037 A | 10/1993 | Bitdinger |
| 5,279,581 A | 1/1994 | Firth et al. |
| 5,322,515 A | 6/1994 | Karas et al. |
| 5,324,272 A | 6/1994 | Smedley et al. |
| 5,328,482 A | 7/1994 | Sircom et al. |
| 5,342,309 A | 8/1994 | Hausser |
| 5,344,404 A | 9/1994 | Benson |
| 5,344,407 A | 9/1994 | Ryan |
| 5,344,417 A | 9/1994 | Wadsworth, Jr. |
| 5,380,286 A | 1/1995 | van den Haak |
| 5,382,241 A | 1/1995 | Choudhury et al. |
| 5,385,555 A | 1/1995 | Hausser |
| D355,970 S | 2/1995 | Monthony et al. |
| 5,433,711 A | 7/1995 | Balaban et al. |
| 5,437,639 A | 8/1995 | Malenchek |
| 5,478,316 A | 12/1995 | Bitdinger et al. |
| 5,498,243 A | 3/1996 | Vallelunga et al. |
| 5,533,980 A | 7/1996 | Sweeney et al. |
| 5,624,400 A | 4/1997 | Firth et al. |
| 5,624,405 A | 4/1997 | Futagawa et al. |
| 5,634,906 A * | 6/1997 | Haber et al. ............... 604/136 |
| 5,647,849 A | 7/1997 | Kalin |
| 5,658,254 A | 8/1997 | Reichenbach et al. |
| 5,733,264 A | 3/1998 | Flowers |
| 5,746,733 A | 5/1998 | Capaccio et al. |
| D403,761 S | 1/1999 | Adams |
| 5,858,008 A | 1/1999 | Capaccio |
| 5,944,699 A | 8/1999 | Barrelle et al. |
| 5,980,495 A | 11/1999 | Heinz et al. |
| D419,671 S | 1/2000 | Jansen |
| 6,027,482 A | 2/2000 | Imbert |
| 6,093,174 A | 7/2000 | Novinkov |
| D429,812 S | 8/2000 | Hjertman et al. |
| 6,126,644 A | 10/2000 | Naganuma et al. |
| 6,186,980 B1 | 2/2001 | Brunel |
| 6,190,364 B1 | 2/2001 | Imbert |
| 6,193,688 B1 | 2/2001 | Balestracci et al. |
| 6,196,998 B1 | 3/2001 | Jansen et al. |
| 6,210,374 B1 | 4/2001 | Malencheck |
| 6,280,421 B1 | 8/2001 | Kirchhofer et al. |
| 6,352,522 B1 | 3/2002 | Kim et al. |
| D460,178 S | 7/2002 | Courteix |
| 6,436,075 B1 | 8/2002 | Liao |
| 6,491,667 B1 | 12/2002 | Keane et al. |
| D469,178 S | 1/2003 | Courteix |
| 6,520,935 B1 | 2/2003 | Jansen et al. |
| D479,270 S | 9/2003 | Strong |
| D479,600 S | 9/2003 | Bainton |
| 6,622,721 B2 | 9/2003 | Vedrine et al. |
| 6,629,963 B2 | 10/2003 | Prais et al. |
| 6,632,199 B1 | 10/2003 | Tucker et al. |
| D484,243 S | 12/2003 | Ryan et al. |
| 6,719,732 B2 | 4/2004 | Courteix |
| 6,776,777 B2 | 8/2004 | Barrelle |
| 6,821,268 B2 | 11/2004 | Balestracci |
| D506,549 S | 6/2005 | Woods |
| 6,936,034 B2 | 8/2005 | Watkins |
| 6,966,897 B2 | 11/2005 | Shimazaki |
| 7,041,087 B2 | 5/2006 | Henderson et al. |
| 7,044,125 B2 | 5/2006 | Vedrine et al. |
| 7,094,223 B2 | 8/2006 | Brunel |
| 7,094,224 B2 * | 8/2006 | Lourenco et al. ............. 604/227 |
| D543,273 S | 5/2007 | Young et al. |
| 7,241,275 B2 | 7/2007 | Alchas et al. |
| 7,255,689 B2 | 8/2007 | Westbye |
| D550,363 S | 9/2007 | Hannant et al. |
| 7,273,484 B2 | 9/2007 | Thoes et al. |
| D563,549 S | 3/2008 | Mulhauser et al. |
| D574,954 S | 8/2008 | Smith |
| D580,052 S | 11/2008 | White |
| D581,046 S | 11/2008 | Sudo |
| D581,049 S | 11/2008 | Sudo |
| D595,406 S | 6/2009 | Kawamura |
| D596,289 S | 7/2009 | Kawamura |
| D598,543 S | 8/2009 | Vogel et al. |
| D604,839 S | 11/2009 | Crawford et al. |
| D606,190 S | 12/2009 | Pruitt et al. |
| D608,885 S | 1/2010 | Sneddon et al. |
| D609,333 S | 2/2010 | Holmes |
| D641,078 S | 7/2011 | Morgan et al. |
| 7,985,216 B2 | 7/2011 | Daily et al. |
| D649,632 S | 11/2011 | Morgan et al. |
| D653,336 S | 1/2012 | Morgan et al. |
| D655,001 S | 2/2012 | Becker et al. |
| D660,419 S | 5/2012 | Morgan et al. |
| D660,958 S | 5/2012 | McLoughlin et al. |
| D661,389 S | 6/2012 | Morgan et al. |
| D676,552 S | 2/2013 | McLoughlin et al. |
| 8,579,866 B2 * | 11/2013 | Morgan et al. ................ 604/187 |
| 2002/0068908 A1 | 6/2002 | Sun |
| 2003/0060777 A1 | 3/2003 | Benz et al. |
| 2003/0181859 A1 | 9/2003 | Brunel |
| 2004/0199124 A1 | 10/2004 | Conte |
| 2005/0240160 A1 | 10/2005 | Lin |
| 2005/0288625 A1 | 12/2005 | Rossback et al. |
| 2006/0178644 A1 | 8/2006 | Reynolds |
| 2007/0078409 A1 | 4/2007 | Saltz |
| 2007/0156100 A1 | 7/2007 | Moesli et al. |
| 2007/0250016 A1 | 10/2007 | Pech et al. |
| 2008/0200881 A1 | 8/2008 | Emmott et al. |
| 2009/0018604 A1 | 1/2009 | Mitelberg et al. |
| 2009/0054849 A1 * | 2/2009 | Burnell et al. ............. 604/198 |
| 2009/0198192 A1 | 8/2009 | Uematsu et al. |
| 2009/0227956 A1 | 9/2009 | Emmott et al. |
| 2009/0299378 A1 | 12/2009 | Knopp |
| 2009/0326477 A1 * | 12/2009 | Liversidge ................ 604/198 |
| 2010/0057080 A1 | 3/2010 | West et al. |
| 2010/0174236 A1 | 7/2010 | Burns et al. |
| 2010/0204707 A1 | 8/2010 | Tanaka et al. |
| 2010/0217205 A1 | 8/2010 | Chevallier et al. |
| 2010/0318030 A1 | 12/2010 | Jenkins |
| 2011/0028909 A1 | 2/2011 | Lum et al. |
| 2011/0028982 A1 | 2/2011 | Lacy |
| 2011/0054440 A1 | 3/2011 | Lewis |
| 2012/0232491 A1 * | 9/2012 | Jennings .................. 604/192 |

FOREIGN PATENT DOCUMENTS

| | | |
|---|---|---|
| GB | 2 424 836 | 10/2006 |
| GB | 2 438 590 | 12/2007 |
| GB | 2438590 A * | 12/2007 |
| GB | 2438593 A * | 12/2007 |
| JP | 2005512637 | 5/2005 |
| JP | 2005-287676 | 10/2005 |
| WO | WO 88/06462 | 9/1988 |
| WO | WO 00/35519 | 6/2000 |
| WO | WO 02/11799 | 2/2002 |
| WO | WO 03/051423 | 6/2003 |
| WO | WO 2004/096324 | 11/2004 |
| WO | WO 2005/032627 | 4/2005 |
| WO | WO 2005/115508 | 12/2005 |

* cited by examiner

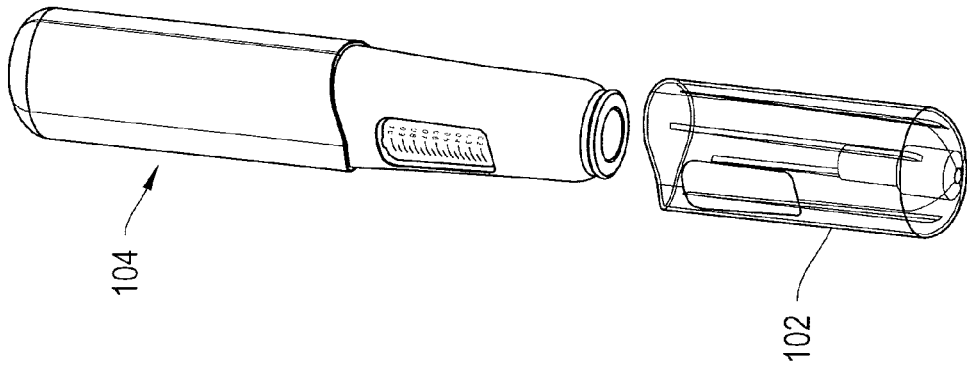
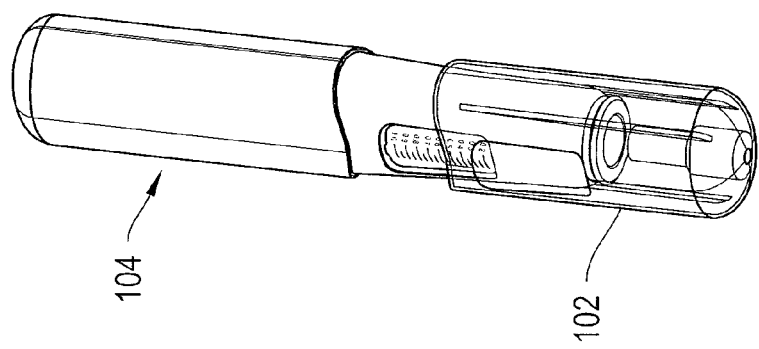
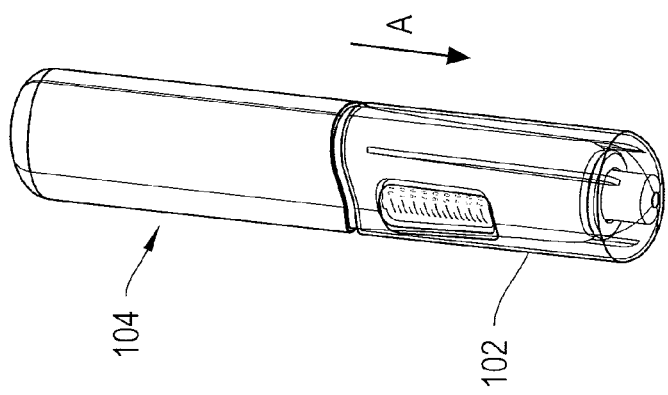

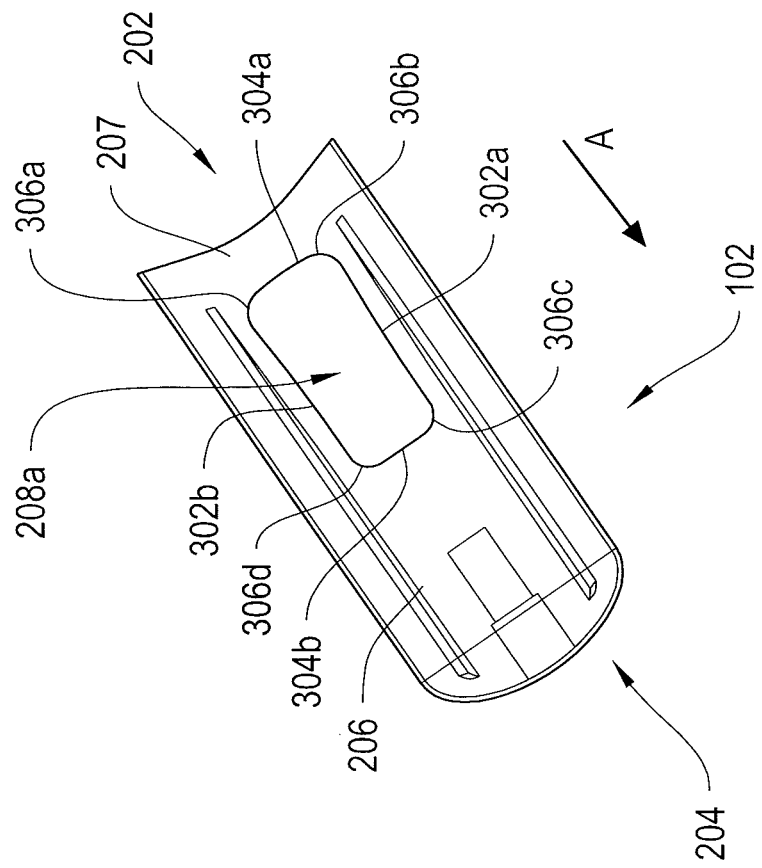
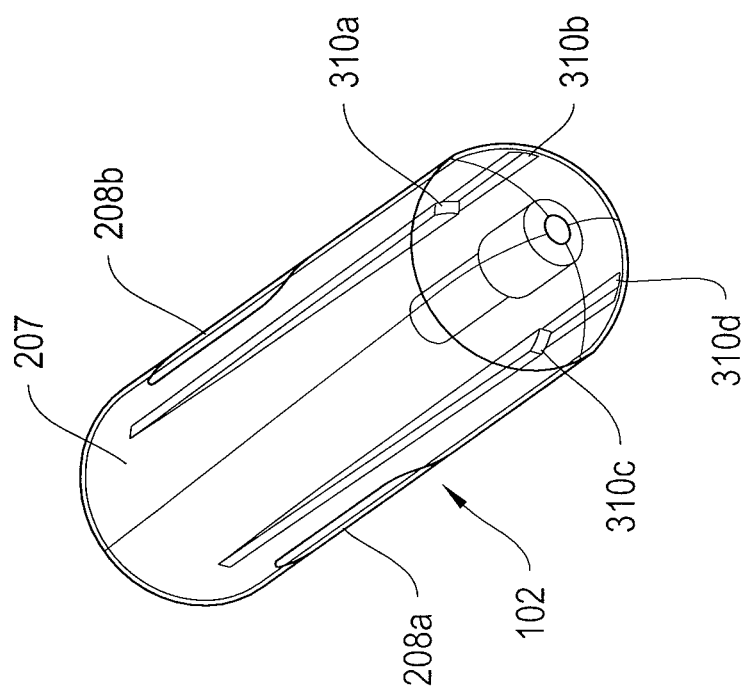
FIG. 3B
FIG. 3A

SECTION A-A

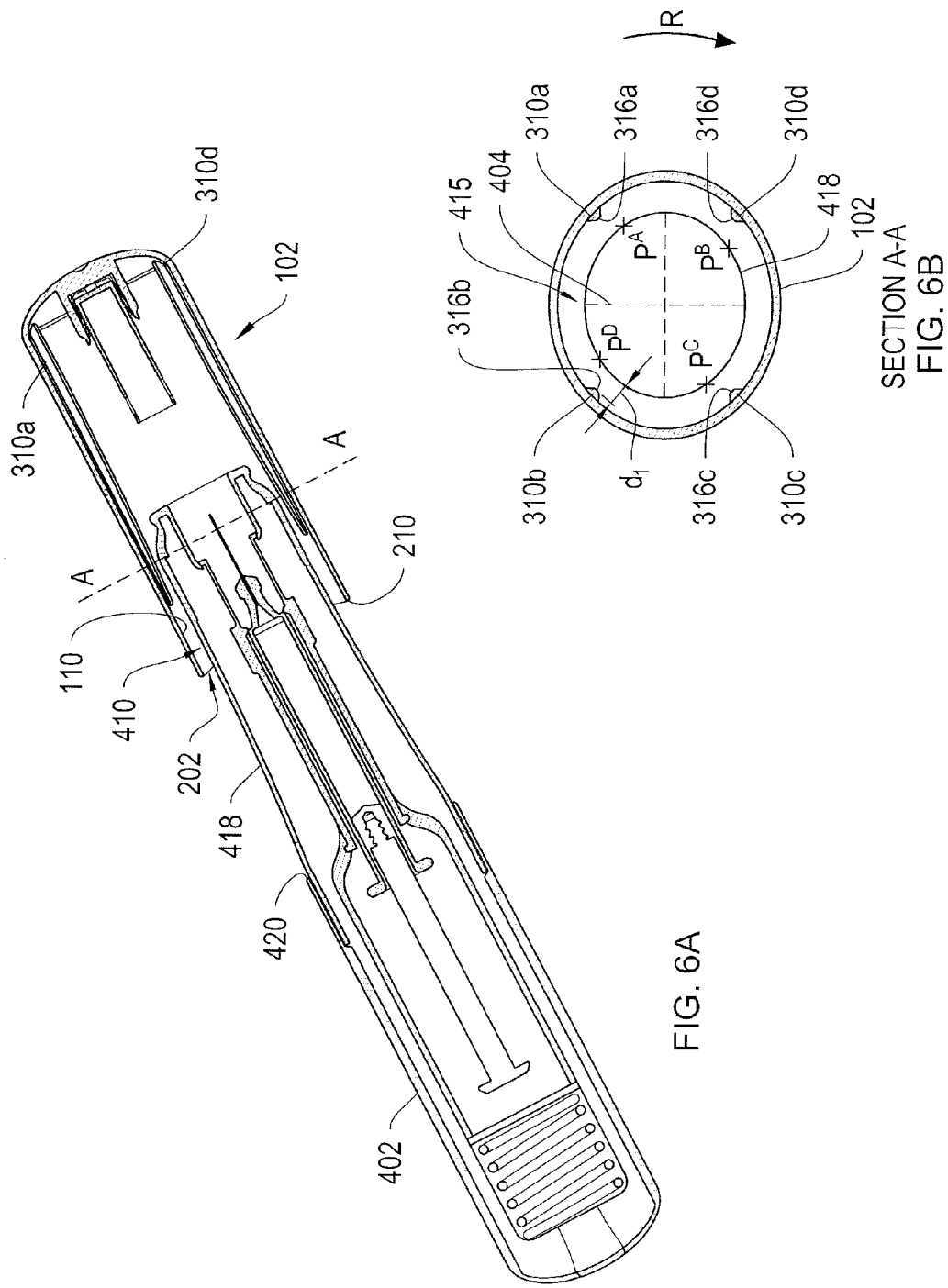

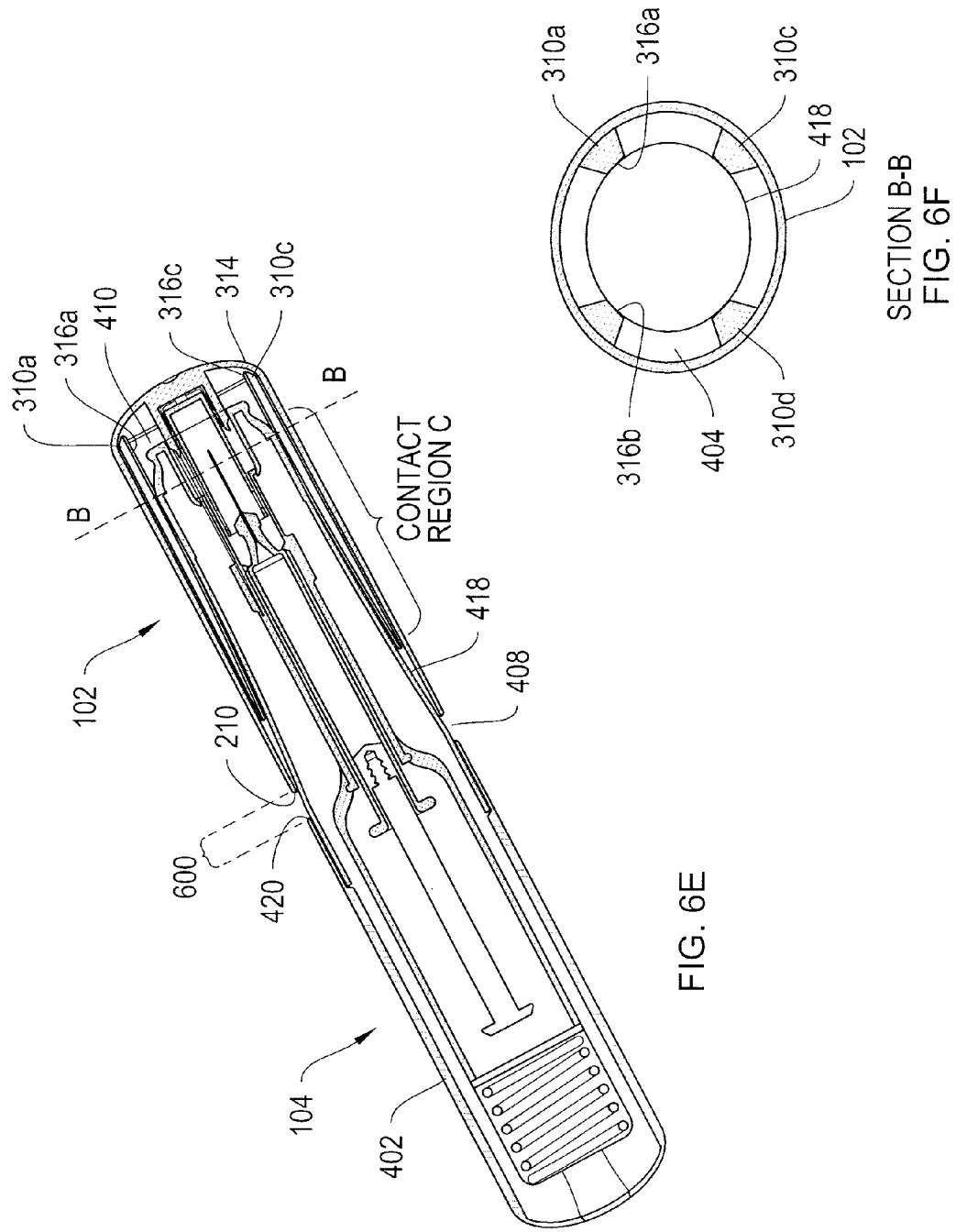

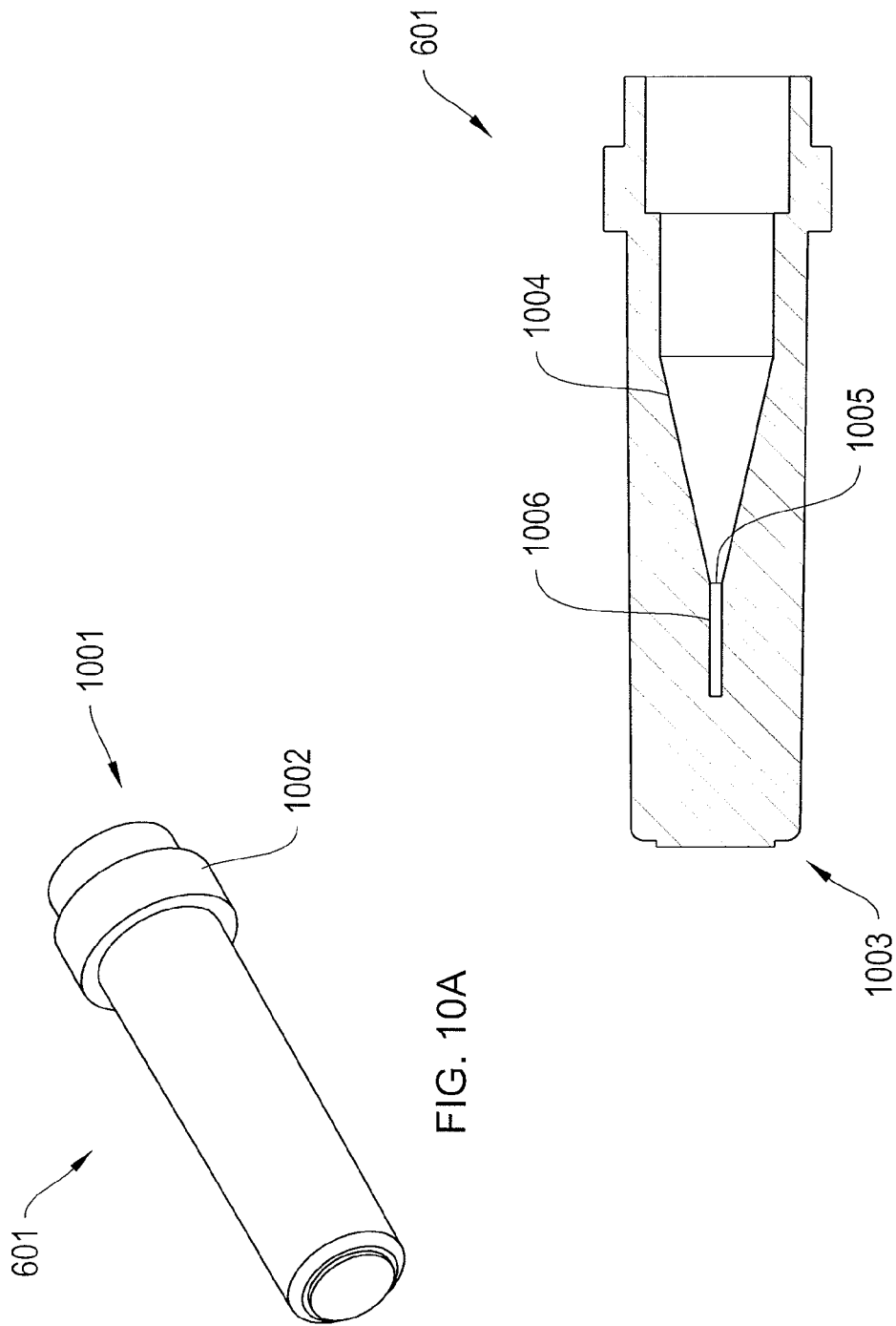

US 8,945,067 B2

SYSTEMS FOR ADMINISTERING MEDICATION

RELATED APPLICATIONS

This application claims the benefit of priority of U.S. provisional application Ser. No. 61/135,262 filed Jul. 18, 2008, and U.S. provisional application Ser. No. 61/192,551 filed Sep. 18, 2008. The disclosures of each of the foregoing applications are hereby incorporated by reference in their entirety.

BACKGROUND

Rheumatoid arthritis ("RA") is an autoimmune disease characterized by chronic inflammation of the joints leading to progressive cartilage destruction and bone erosion. Patients with RA often suffer from inflamed joints with joint pain, stiffness, and swelling. More advanced forms of inflammation may cause the joint to lose its shape, alignment, and movement. RA has been treated for many years with a variety of medicines such as steroids and disease modifying antirheumatic drugs (DMARDs). Some of these drugs are administered through injections or infusions. However, it is difficult for RA patients with compromised joint strength and mobility to manipulate available syringes to perform a self injection, particularly for viscous biologics and other drugs. Currently, some drugs are injected using conventional hypodermic syringes with a small needle cap. The conventional syringes are generally small, which makes holding or manipulating the syringe more difficult. Many of these syringes also do not provide patients with satisfactory handling and gripping structures.

In addition, typical syringes are difficult for some patients to de-cap and re-cap. Such syringes are difficult to manipulate, particularly patients suffering from joint swelling and pain as they must force their fingers to close in around a small needle cap to manipulate the cap.

Some medications are injected using an autoinjector. Standard autoinjectors include a small pen-cap like cap that houses a rubber needle cover that shields the needle of the device. Exemplary autoinjectors available today include HUMIRA® Pen and Enbrel SureClick®. However, in certain instances, the cap, when disengaged by the patient, fails to remove the rubber needle cover shielding the needle of the device. The patient then attempts to remove the rubber needle cover, which may lead to accidental needle stabs. As one can imagine, failing to remove the rubber needle cover exposes the patient to great danger and inconvenience. Certain autoinjectors also house the medication within an enclosed housing and do not provide a mechanism for viewing the volumetric level or color of the medication inside, thereby impairing the patient from confirming whether or not the right medication level is included in the autoinjector.

A more user friendly medication administering system is needed to address these and other problems posed by currently available autoinjector systems. There is a particular need for an autoinjector system that allows a patient to more easily administer a viscous drug, yet still provide increased safety as well as increased control. There is also a need for an autoinjector system that provides more ergonomic cap removing capabilities for patients with joint pain.

SUMMARY OF THE INVENTION

The autoinjector system disclosed herein addresses various deficiencies in the prior art by providing, in various aspects and embodiments, an improved autoinjector system that allows patients to more easily administer medicine, particularly patients with compromised dexterity or joint strength. In one representative embodiment, an autoinjector device is provided with a housing, a syringe assembly that is slidably mounted on the housing and having a needle and a fluid container, an autoinjector actuator for urging the syringe assembly with respect to the housing from a storage position to a launch position, and an improved cap that releasably engages with the housing. The cap includes a protruding pocket for receiving a needle cap remover. Exemplary needle cap removers include a connector having a base, a plurality of first legs spaced symmetrically away from one another and extending proximally from the base, and a plurality of second legs extending proximally from the base and having a tip that flares outwardly towards the protruding pocket. At least one of the second legs is positioned between two of the first legs.

In certain embodiments, a first leg includes internally facing barbs that engage a needle shield that covers the needle of the syringe assembly. In certain embodiments, the internally facing barbs include a tip that flares inward and towards the base. In certain embodiments, the tip of at least one of the first legs dig into the needle shield. The tip of at least one of the second legs engages the protruding pocket. In certain embodiments, the internally facing barbs are concaved. The internally facing barbs may also extend at an angle with respect to the upright. In certain embodiments, at least one of the first legs includes an upright and a first pair of internally facing barb tips positioned to a lateral side of the upright and a second pair of internally facing barb tips positioned to a medial side of the upright.

According to one implementation, an autoinjector device includes a housing having distal and proximal ends, the distal end including an interfacing passage that receives a needle cap. The needle cap releasably engages with the housing and has a protruding pocket for receiving a needle cap remover. In certain implementations, a syringe assembly is provided that slidably mounts on the housing and includes a needle and a fluid container. Exemplary implementations also include an autoinjector actuating mechanism disposed on the housing for urging the syringe assembly with respect to the housing from a storage position to a launch position, where when the syringe assembly is in the storage position, the protruding pocket of the cap extends through the interfacing passage, and when the syringe assembly is in the launch position, the needle of the syringe assembly extends through the interfacing passage. In certain embodiments, the autoinjector device includes a needle cap remover having a connector that includes a base, a plurality of first legs spaced symmetrically away from one another and extending proximally from the base, and a plurality of second legs extending proximally from the base and having a tip that flares outwardly towards the protruding pocket. At least one of the second legs is positioned between the plurality of the first legs. In certain embodiments, the connector receives a needle cover. In certain embodiments, the autoinjector actuating mechanism includes a spring. In certain embodiments, the cap covers about half of the length of the device.

In certain embodiments, the needle cap includes closed and open ends, where the needle cap includes a clear window disposed between the closed and open ends. The housing may also include a corresponding window positioned beneath the clear window of the needle cap when the cap is engaged to the housing. In certain embodiments, the needle cap includes longitudinal ribs extending along the length of the cap. The longitudinal ribs may also extend within the needle cap. The longitudinal ribs may be spaced apart so that at least one rib extends on one side of a clear window and at least one rib extends on another side of the clear window. In certain embodiments, the needle cap includes a curved interface and the housing includes a corresponding interface adapted to mate with the curved interface of the needle cap.

BRIEF DESCRIPTION OF THE DRAWINGS

The following Figures depict illustrative embodiments of the invention in which like reference numerals refer to like elements. These depicted embodiments may not be drawn to scale and are to be understood as illustrative and not limiting.

FIGS. 2A-2D depict perspective views of an elongate cap disengaging from a housing of the autoinjector depicted in FIG. 1A.

FIGS. 3A-3D depict various views of an exemplary embodiment of an elongate cap of the autoinjector depicted in FIG. 1A.

FIGS. 6A-6C depict various views of an elongate cap engaging a lower housing of the autoinjector according to an illustrative embodiment of the invention.

FIGS. 6E-6F depict longitudinal and transverse cross sectional views of an elongate cap engaging a lower housing according to an illustrative embodiment of the invention.

FIGS. 10A-10B depict perspective and cross sectional views of an exemplary embodiment of the needle shield depicted in FIG. 9B.

DESCRIPTION OF EXEMPLARY EMBODIMENTS

To provide an overall understanding of the invention, certain illustrative embodiments will now be described, including exemplary embodiments of a system that is adaptable to automatically inject drugs in the treatment of a patient suffering RA or other auto-immune diseases such as Multiple Sclerosis, Lupus, and Spondylitis. However, it will be understood by one of ordinary skill in the art that the systems and methods described herein can be adapted and modified for other suitable applications and that such other additions and modifications will not depart from the scope hereof.

Figure 1A:
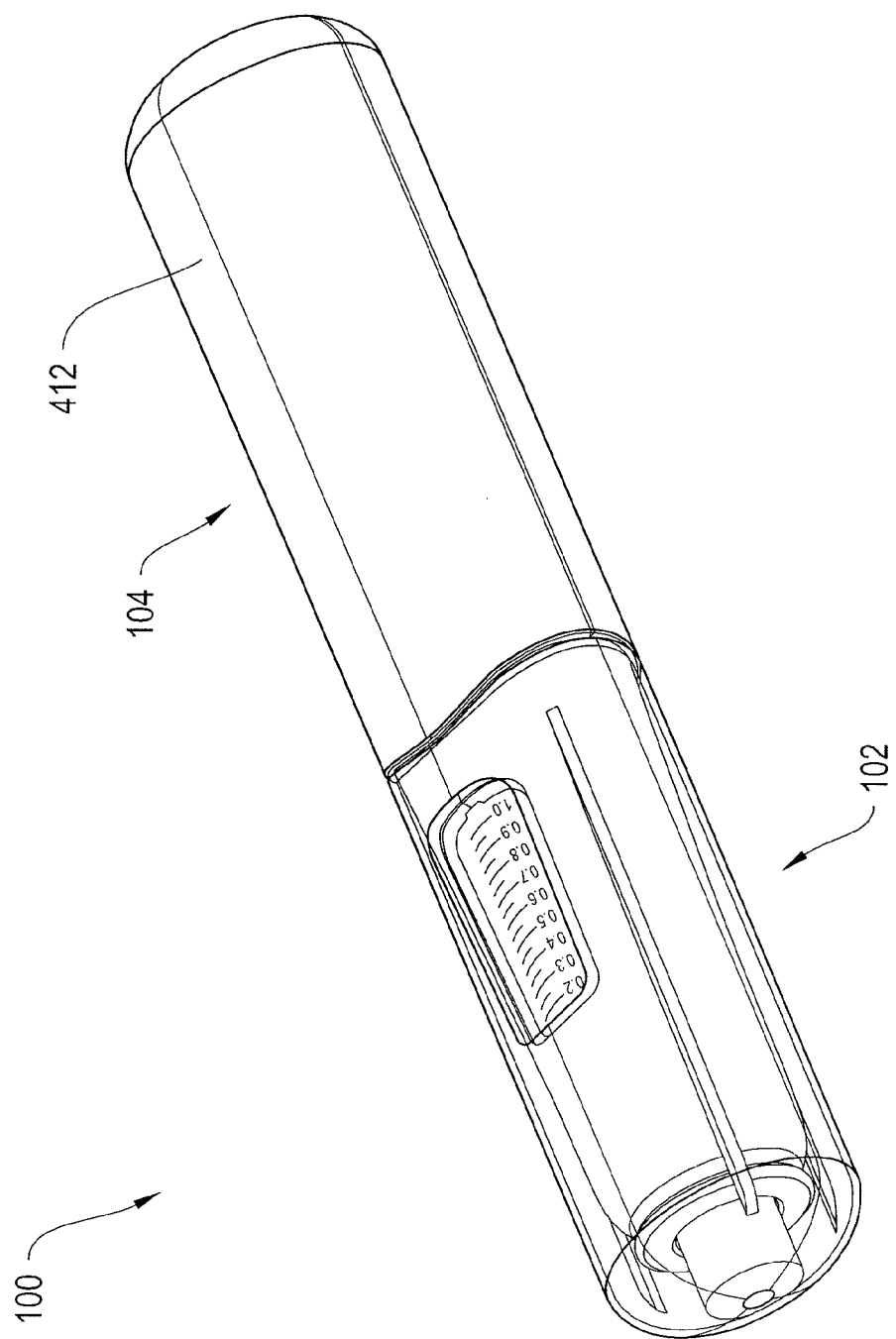
FIG. 1A depicts a perspective view of an autoinjector system in a storage position according to an illustrative embodiment of the invention.
Figure 1B:
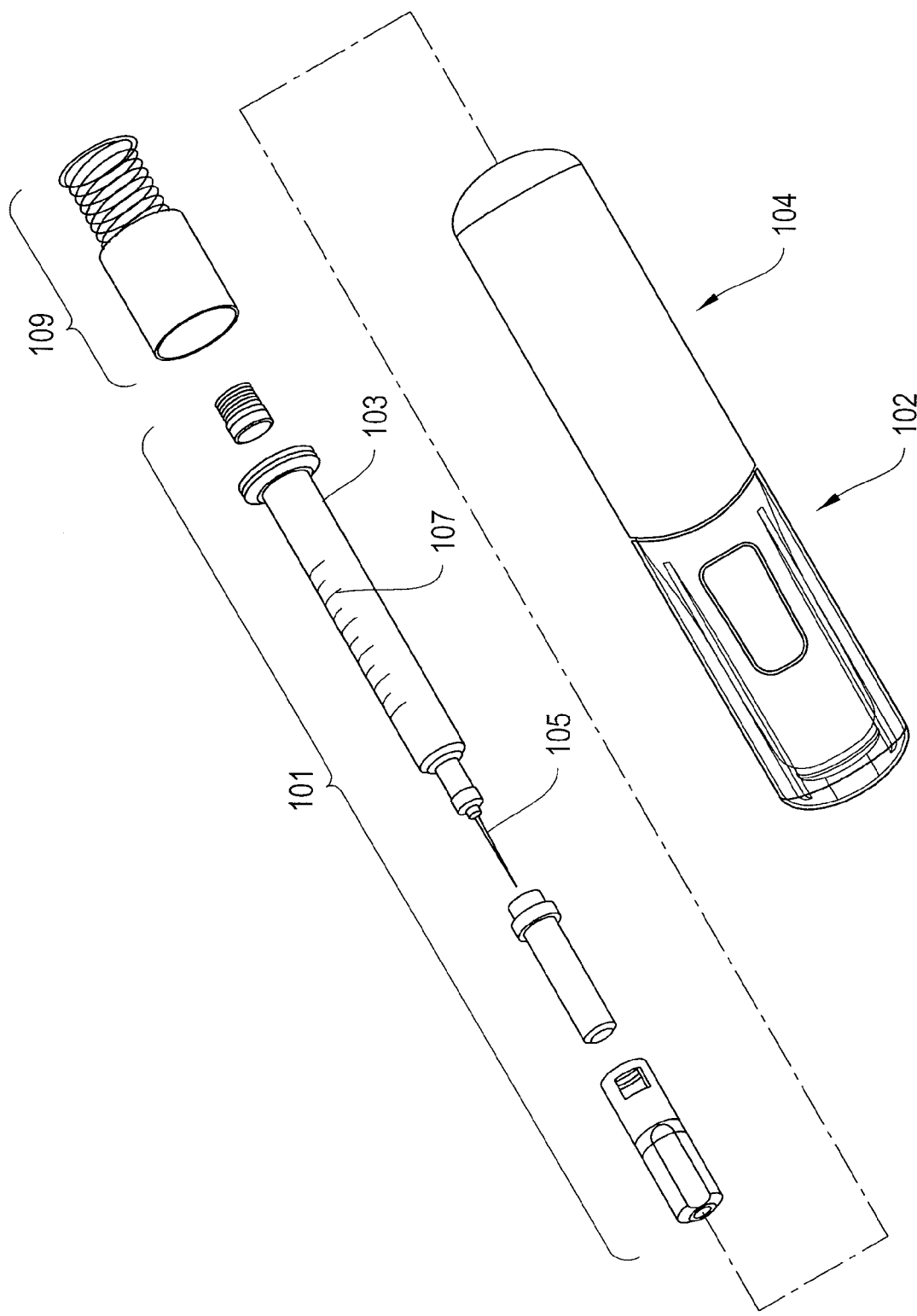
FIG. 1B depicts an exploded view of the autoinjector system shown in FIG. 1A.

Turning to the illustrative embodiments, FIGS. 1A-1B show perspective and exploded views of an exemplary embodiment of an autoinjector system 100. As shown, the autoinjector system 100 includes an elongate cap 102 that is releasably secured to a housing 104. The housing 104 provides a grasping surface 412 to allow a patient to hold and inject the medication contained in the autoinjector system 100. As shown, the elongate cap 102 and the grasping surface 412 of the housing 104 have contrasting finishes so the patient can easily identify the grasping surface 412 from the elongate cap 102 that needs to be removed prior to use.

FIG. 1B is an exploded view of the autoinjector system 100 showing the housing 104 ready to receive a syringe assembly 101 that is slidably mounted within the housing 104. The syringe assembly 101 includes a needle 105 and a medication container 103. The housing 104 also includes, among other things, an actuating mechanism 109 for urging the syringe assembly 101 with respect to the housing 104 from a storage position (FIG. 1) to a launch position (FIG. 8) to allow automatic dispensing of the medication contained within the syringe assembly 101. As shown, the actuating mechanism 109 is spring loaded, however, any type of an energy source may be used with the device described herein. For example, a gas cylinder similar to the type used in a conventional aerosol can or the like (i.e., having a valve through which gas can be released at will and in a controlled manner) can be used. Once mated, the syringe assembly 101 is completely enclosed within the housing 104 and only the dosage marks 107 disposed on the medication container 103 are visible from the outside (See FIG. 1).

Figure 2D:
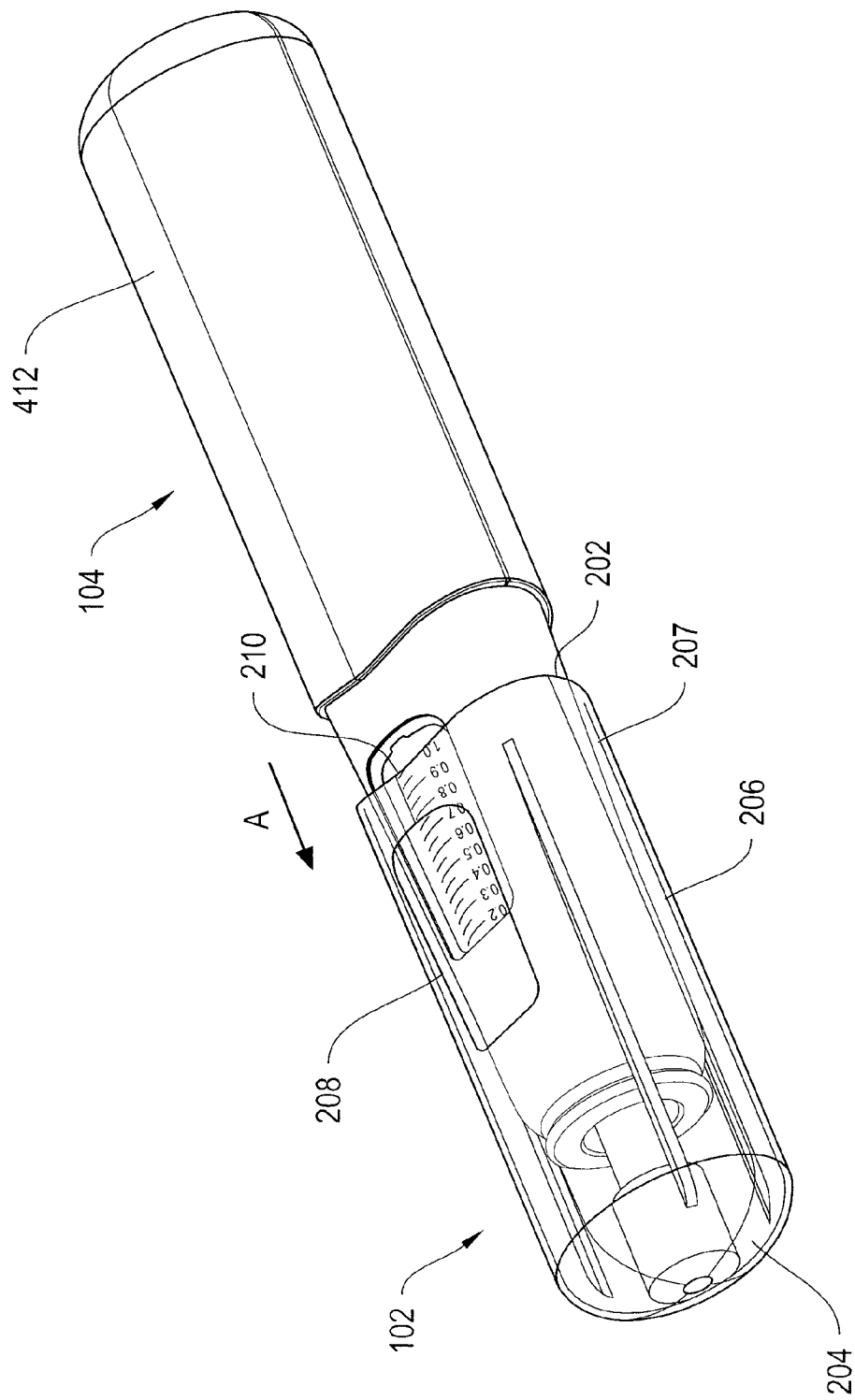

As noted above, the elongate cap 102 is releasably engaged to the housing 104 for shielding a portion of the housing 104 prior to use. The elongate cap 102 is held onto the housing 104 via friction, thus a small force sufficient to overcome the holding friction is applied to disengage the elongate cap 102 from the housing 104. FIGS. 2A-2C show the elongate cap 102 being disengaged from the housing 104 at various points, which occurs as the elongate cap 102 is pulled distally away from the housing 104 in a direction noted by Arrow A. As shown in FIG. 2D, the elongate cap 102 has an open end 202 and a closed end 204 and includes, among other things, a sleeve body 206 and a proximal rim 210 positioned at the open end 202 of the elongate cap 102. As illustrated, the length of the elongate cap 102 extends substantially along the shaft of the autoinjector 100, covering up to about half of the length of the autoinjector 100 (FIG. 1). This allows a patient with joint pain to use a full hand grip to grasp and remove the elongate cap 102. Compared to a shorter or smaller cap, the longer length of the elongate cap 102 allows the patient to grasp more of the elongate cap 102 using various grasping techniques to accommodate their reduced hand dexterity and/or strength. In certain embodiments, the elongate cap 102 is longer than about the half of the length of the autoinjector 100.

A patient holding the autoinjector 100, through the clear window 208, can visually check the drug (e.g., color or presence of other substance contained within the syringe assembly) and its volumetric level. As shown, the elongate cap 102 is semi-transparent on all areas other than the clear window 208. In some embodiments, the outer surface 207 of the sleeve body 206 has a frosted finish to hide the inner components, which provides an aesthetically pleasing look to the autoinjector. The frosted outer surface 207 also allows the patient to easily distinguish by feel the elongate cap 102 from the housing 104 of the autoinjector 100. In certain embodiments, the grasping surface 412 of the housing 104 includes a rubber texture for providing friction when gripped by the patient, which reduces slipping of the handle while the device is in use.

Figures 3C, 3D:
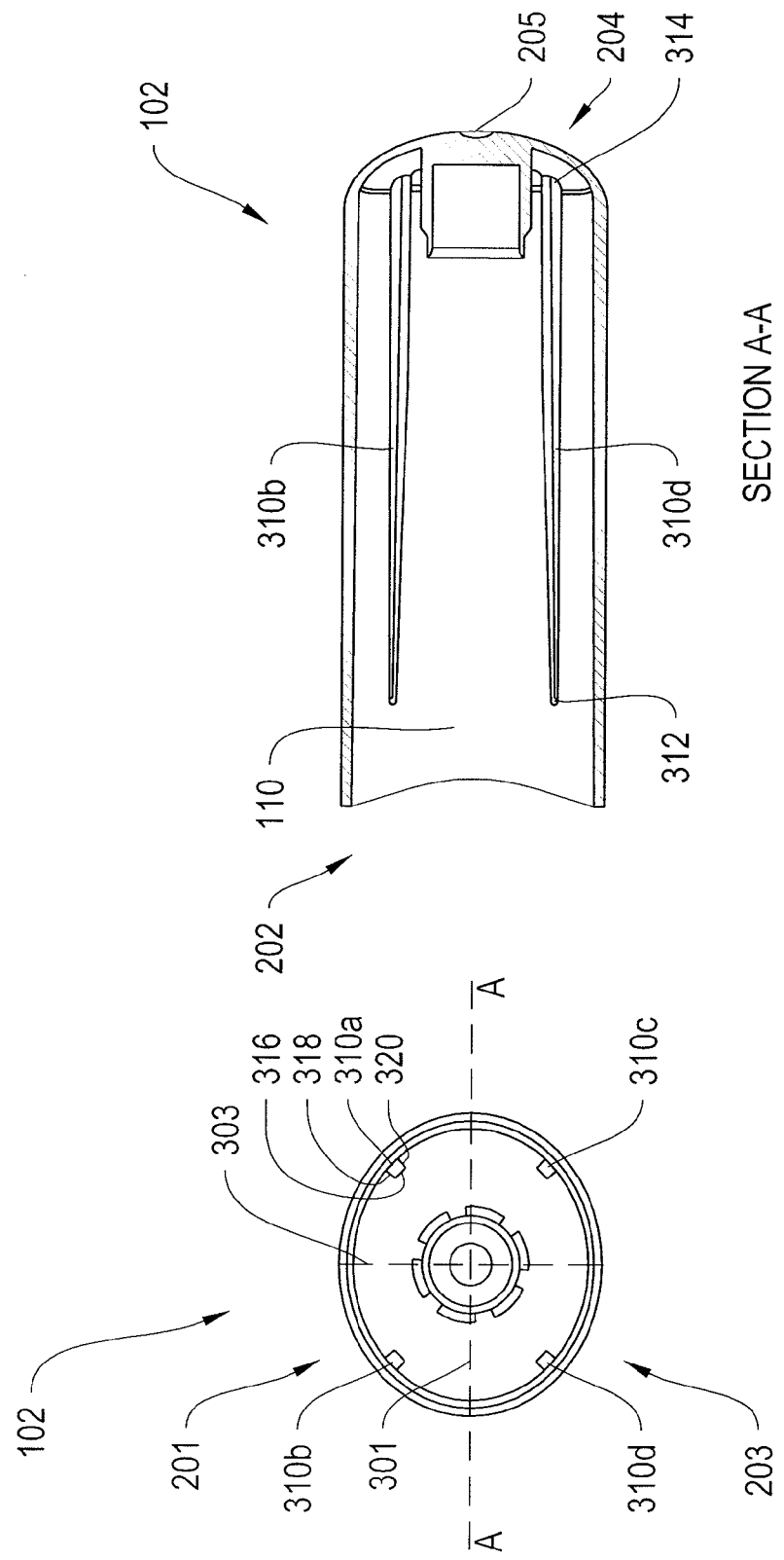

FIGS. 3A-3D show various views of the elongate cap 102, an elliptical cylinder, that has an elliptical cross section as shown in FIG. 3C. FIG. 3A shows the elongate cap 102 having two clear windows 208a and 208b positioned facing one another. This allows the patient to hold the autoinjector 100 and check the content of the autoinjector 100 regardless of the direction that the autoinjector 100 is being held. As shown in FIG. 3B, the clear window 208a is disposed on the outer surface 207 between the open end 202 and the closed end 204 of the elongate cap 102. This window allows the patient to inspect the content disposed beneath the clear window 208a. The patient can inspect the drug prior to and without having to disengage the elongate cap 102 from the housing 104, thereby reducing the risk of contamination that might otherwise occur if the patient removed the cap to view the contents of the injector. It may also reduce the likelihood of the patient accidentally stabbing herself while checking the amount or presence of the drug contained within the housing while the cap is removed.

As shown in FIG. 3B, the clear window 208a includes first and second longitudinal sides 302a-302b and first and second transverse sides 304a-304b. The longitudinal sides 302a302b taper towards one another along Arrow A as they extend from the first transverse side 304a to the second transverse side 304b. The ends of the longitudinal sides 302a-302b and transverse sides 304a-304b are curved so that the clear window 208a has four rounded corners 306a-306d. The shape and the size of the clear window 208a may vary depending on the size and the shape of a drug containing compartment. For example, the clear windows 208a and 208b may be rectangular, square, or oval in shape. In certain embodiments, the clear windows 208a and 208b are formed by removing a section of material of the sleeve body 206. In other embodiments, the clear windows 208a and 208b are made of a clear material such as glass or plastic to allow the patients to view contents underneath the clear windows 208a and 208b.

An inside view of the elongate cap 102 having an elliptical cross section is shown in FIG. 3C. The elongate cap includes major axis (or "diameter") 301 and minor axis (or "diameter") 303, where the major diameter 301 is greater than the minor diameter 303. As shown, the elongate cap 102 includes two upper longitudinal ribs 310a-310b in an upper portion 201 of the elongate cap 102 and two lower longitudinal ribs 310c-310d in a lower portion 203 of the elongate cap 102. Each rib also includes a contacting surface 316 formed by two side surfaces 318 and 320. With respect to the Axis A (FIG. 3C), the two upper longitudinal ribs 310a-310b are disposed opposite the two lower longitudinal ribs 310c-310d. As shown in FIG. 3A, the longitudinal ribs are spaced apart so that at least one rib extends on one side of a clear window 208a and at least one rib extends on opposite side of the clear window 208a. These longitudinal ribs 310a-310d help guide and secure the elongate cap 102 to the housing 104 during the manufacturing assembly and also re-capping process, as discussed below.

As shown in FIG. 3D, which shows a cross sectional view of the elongate cap 102, the longitudinal ribs 310a-310d are disposed on an inner surface 110 of the elongate cap 102 and extend longitudinally along the length of the elongate cap 102. Each longitudinal rib also includes a tip 312 disposed near the proximal open end 202 and a base 314 positioned near the closed distal end 204. Each longitudinal rib tapers gradually along the length of the elongate cap 102 from the base 314 towards the tip 312. The thickness of the longitudinal rib thus varies along the length of the elongate cap 102—the longitudinal rib near the closed end 204 is thicker than near the open end 202. This difference in thickness enables the elongate cap 102 to secure itself to the housing 104, as described more fully with respect to FIGS. 6E-6F.

As illustrated in FIG. 3D, the closed end 204 of the elongate cap 102 is rounded and tapers to a tip region 205. However, the shape of the closed end 204 of the elongate cap 102 may be of any shape that provides structural support to the elongate cap 102. For example, the tip region of the elongate cap may be flat to allow the patient to hold the autoinjector 100 against a flat surface such as a table.

Figure 4:
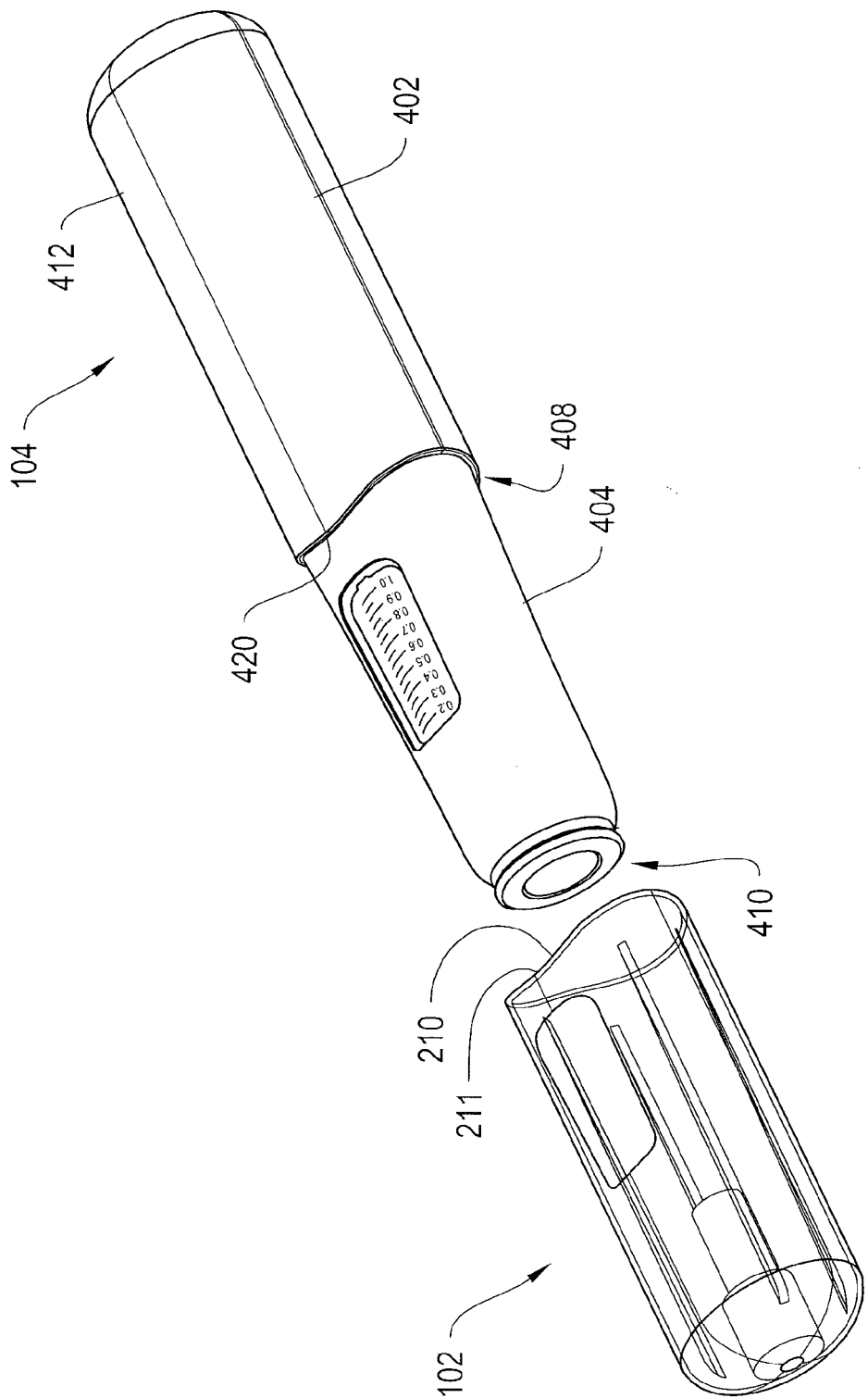
FIG. 4 shows a perspective view of an elongate cap being removed from a housing of the autoinjector depicted in FIG. 1A.

FIG. 4 shows a perspective view of the elongate cap 102 disengaged from the housing 104 (without the syringe assembly, for viewing clarity). As shown, the housing 104 includes an upper handle 402 for providing the grasping surface 412 and a lower housing 404 that encases the syringe assembly 101 (not shown). The lower housing 404 includes a distal end 410 and a proximal end 408 that interfaces with the upper handle 402 as described below.

Figure 5B:
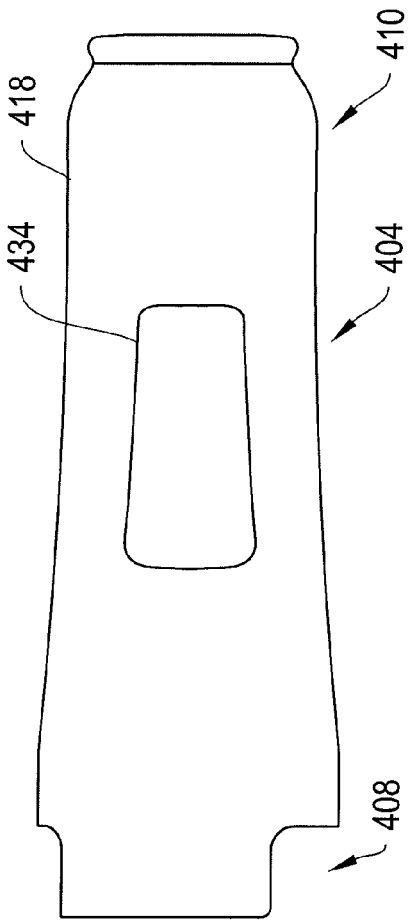
FIGS. 5A-5C depict inside, side, and perspective views of a lower housing of the housing as depicted in FIG. 4.
Figure 5C:
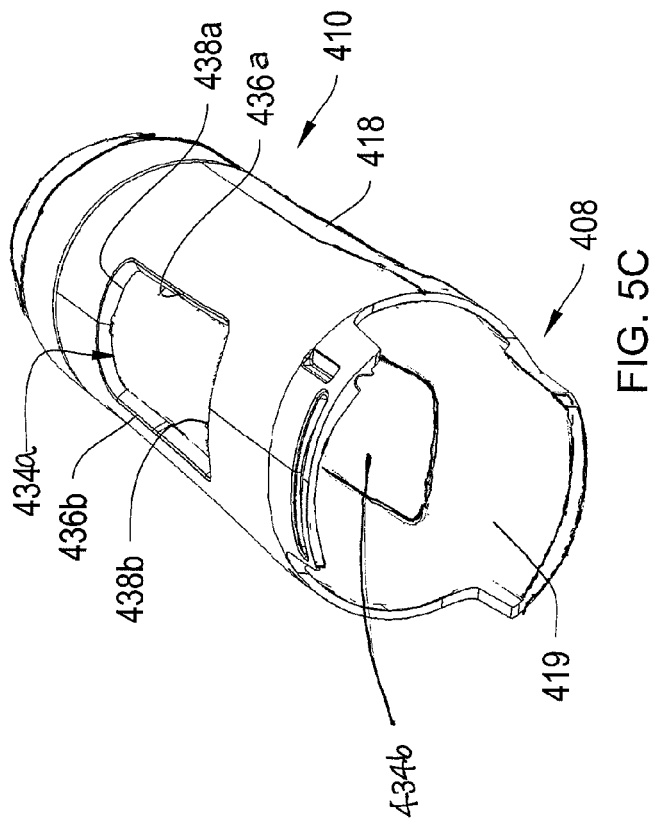
Figure 5A:
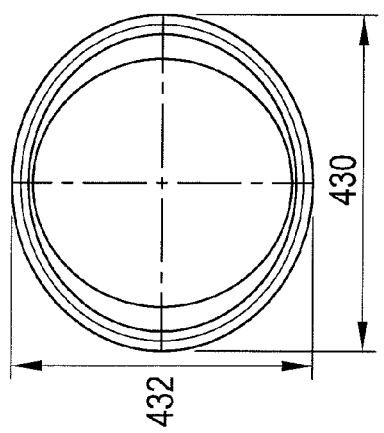

FIGS. 5A-5C show various views of the lower housing 404 having major diameter 430 and minor diameter 432, where the major diameter 430 is longer than the minor diameter 432. As shown, the lower housing 404 is tapered from the proximal end 408 to the distal end 410. The major and the minor diameters gradually increase from the distal end 410 towards the proximal end 408. The lower housing 404 includes two cut out windows 434a and 434b, positioned beneath the elongate cap 102, through which the syringe dosage markings can be viewed. The cut out windows 434a and 434b align with the clear windows 208a and 208b when the elongate cap 102 is fully engaged to the lower housing 404. As noted above, the clear windows 208a and 208b of the elongate cap 102 allow the patient to see through the window and check the drug contained beneath.

Figure 5D:
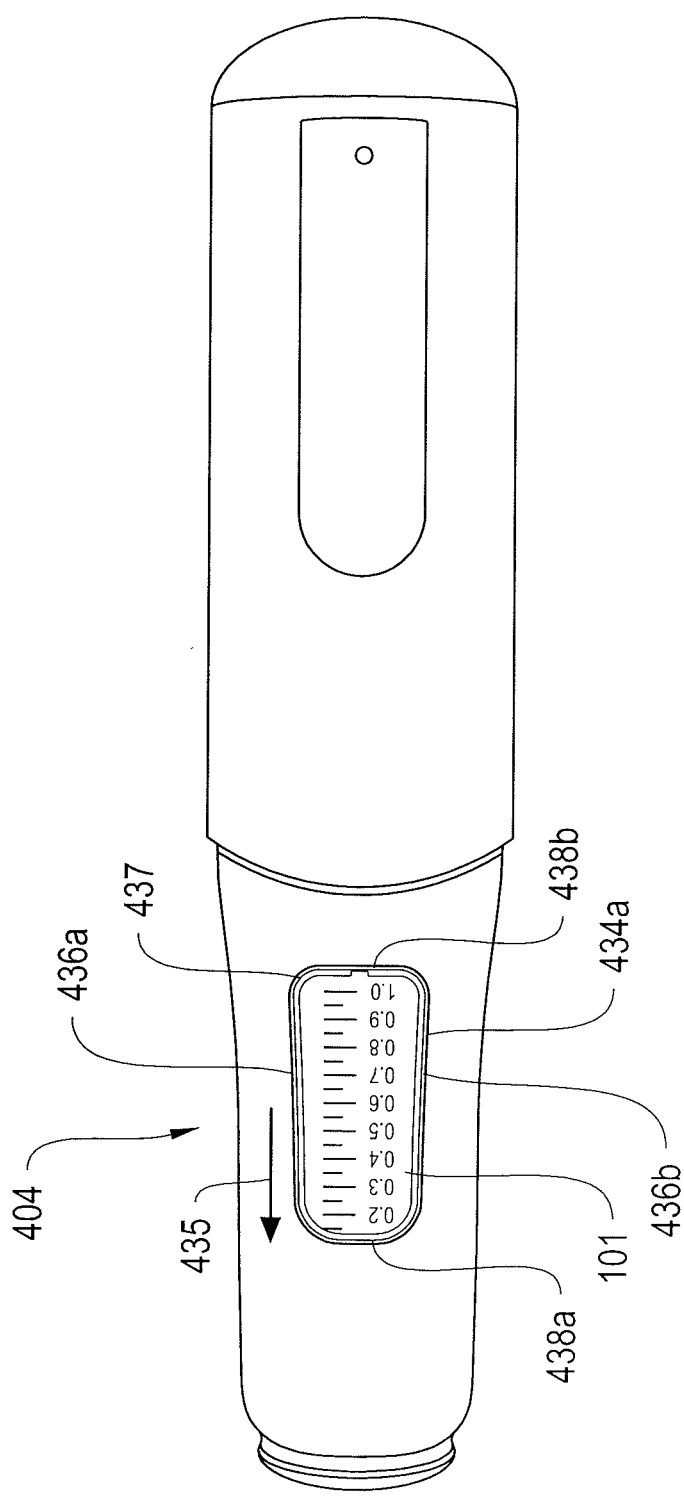
FIG. 5D depicts a housing having a window that displays the medication contained within a syringe assembly disposed within the housing.

As illustrated in FIG. 5C, the cut out window 434a includes a plurality of longitudinal side surfaces 436a-436b, a proximal transverse side surface 438b, and a distal transverse side surface 438a. Each of these surfaces extends from the outer surface 418 to the inner surface 419 at an angle. FIG. 5D shows the syringe assembly 101 fitted within the lower housing 404 and shows the plurality of longitudinal and transverse side surfaces 436a-436b and 438a-438b extending at an angle. As shown, the longitudinal sides surfaces 436a-436b taper towards one another along Arrow 435 as they extend from the proximal transverse side surface 438b to the distal transverse side surface 438a, corresponding in shape with the clear window 208a of the elongate cap 102. As illustrated, the surfaces 436a-436b and 438a-438b are connected to one another to form a single contiguous surface 437 extending around the drug containing portion of the syringe assembly 101. It will be understood by one of ordinary skill in the art that the shape and the size of the cut out window 434 may vary depending on the size and the shape of a drug containing compartment and the corresponding clear window disposed on the elongate cap 102.

In addition to the elongate cap having features discussed above, an improved cap having self-alignment capability is disclosed herein. In some instances, patients attempt to re-cap the elongate cap 102 to the housing 104 after use, even if advised not to do so. Therefore, it is beneficial to have features that allow the patients to more easily manipulate the elongate cap 102 with minimal effort to align the elongate cap 102 with respect to the housing 104. The elongate cap 102 self aligns and secures itself to the lower housing 404 of the housing 104 so that the proximal rim 210 aligns with the distal rim 420 on the upper handle 402 (See FIG. 4). FIGS. 6A-6F illustrate the elongate cap 102 engaging the lower housing 404 to create this alignment.

FIG. 6A shows a cross sectional view of the elongate cap 102 initially engaging the lower housing 404. More specifically, the inner surface 110 of the elongate cap 102, near the open end 202 of the elongate cap 102, loosely friction fits with the outer surface 418 of the lower housing 404 near the distal end 410. Because the elliptical cross sectional area of the lower housing 404 near the distal end 410 is smaller than the elliptical cross sectional area of the elongate cap 102 near the open end 202, the elongate cap 102 is initially loosely overlaid, with even some rotational movement, with respect to the lower housing 404, temporarily misaligning proximal rim 210 of the elongate cap 102 and distal rim 420 of the upper handle 402. As an illustration, FIG. 6B shows a transverse cross sectional view across plane A depicted in FIG. 6A, which shows distance $d_1$ as a space between the contacting surfaces 316a-316d of the elongate cap 102 and the outer surface 418 of the lower housing 404. In this configuration, the elongate cap 102 is able to rotate with respect to the lower housing 404 and the contacting surfaces 316a-316d of the longitudinal ribs 310a-310d do not yet make contact with the outer surface 418 of the lower housing 404, but the outer surface 418 gradually flares outwardly towards the upper handle 402 from the distal end 410 (FIG. 6A). Thus, as the elongate cap 102 is pushed proximally onto the lower housing 404, a right side pair of the longitudinal ribs (formed by the ribs 310a and 310d) and/or a left side pair (formed by the ribs 310b and 310c) impedes the elongate cap 102 from rotating freely and keeps the elongate cap 102 on track while the cap 102 is pushed towards the upper handle 402. More specifically, the right and left pairs of the longitudinal ribs contact the regions $P_A$ to $P_d$ of the flaring outer surface 418, which spatially restricts the elongate cap 102 and prevents it from rotating in the direction R (FIG. 6B), thereby maintaining the orientation of the elongate cap 102 with respect to the lower housing 404. Because the left and right side pairs are spaced on left and right sides of the elongate cap 102, the center region 211 of the proximal rim 210 (FIG. 4) is automatically aligned along the center region 415 (FIG. 6B) of the outer surface 418 of the lower housing 404, thereby being positioned to engage the distal rim 420 of the upper handle 402 for mating upon closure.

Figure 6C:
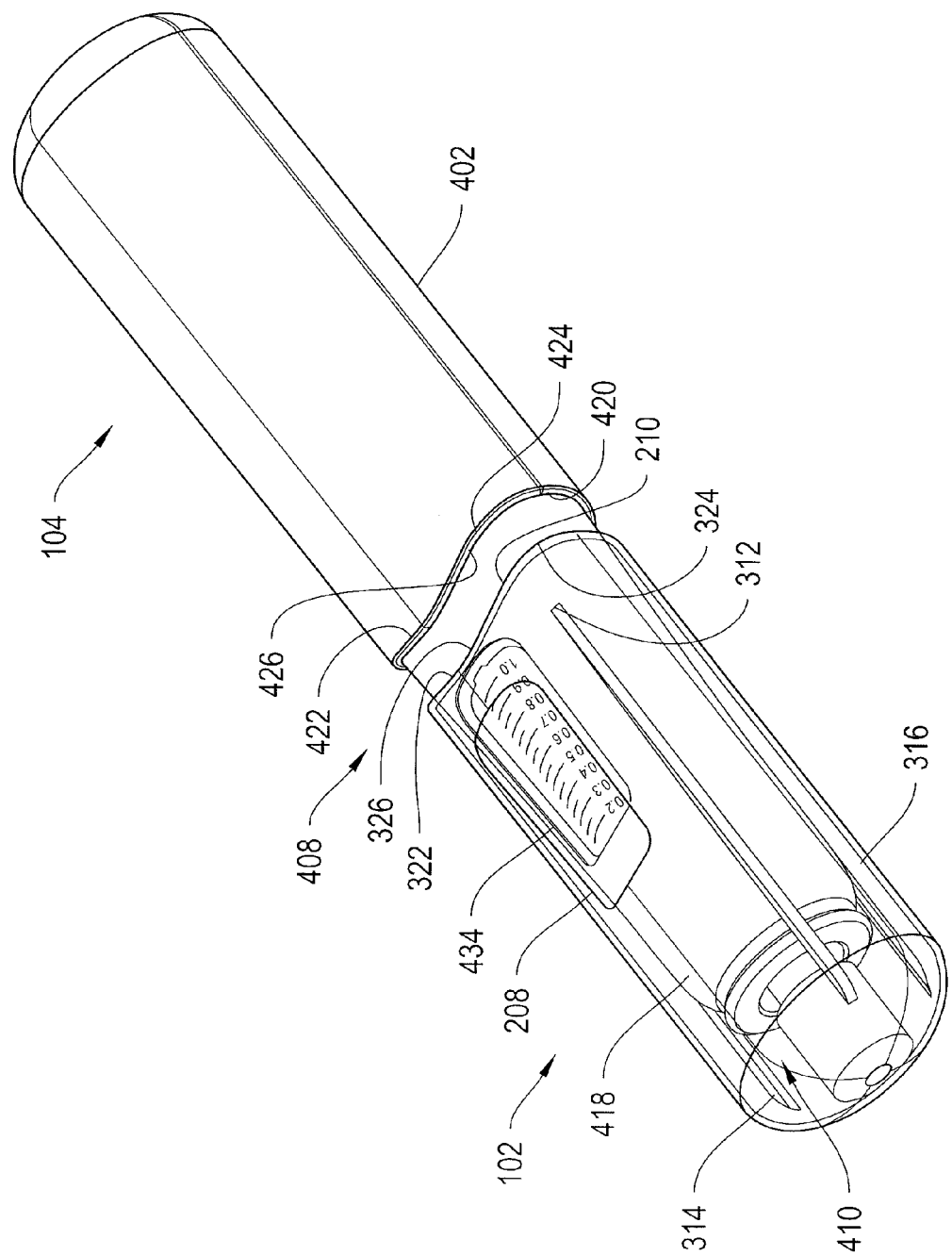

FIG. 6C shows a perspective view of the elongate cap 102 partially covering the lower housing 404 in the course of forming the alignment. As the elongate cap 102 moves closer to the upper handle 402, the proximal rim 210 of the elongate cap 102 and the corresponding distal rim 420 of the upper handle 402 help orient the elongate cap 102 with respect to the upper handle 402. A contoured mating interface 500 (FIG. 6D) is formed when the proximal rim 210 of the cap 102 and the corresponding distal rim 420 of the upper handle 402 are fully mated to one another.

Figure 6D:
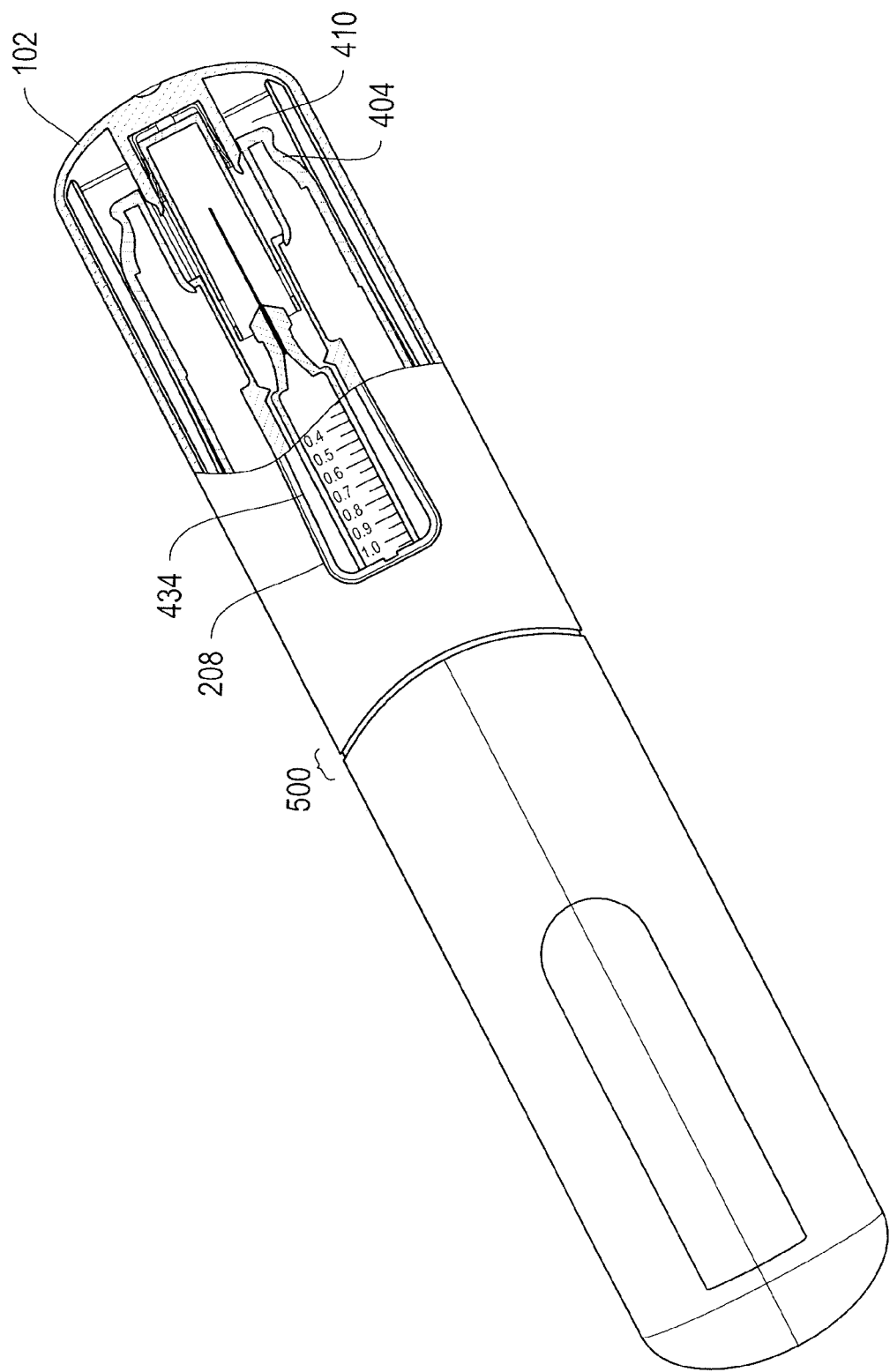
FIG. 6D shows a perspective view of an autoinjector in a storage position with a cross sectional (cut away) view of the distal region of the autoinjector.

Referring again to FIG. 6C, the proximal rim 210 of the elongate cap 102 includes a lower trough 322 and an upper extension 324. These mate with a corresponding lower extension 422 and a corresponding upper trough 424 of the distal rim 420. The curves of the troughs and extensions are so configured to force the troughs 322 and 424 to move toward their respective mating extensions 422 and 324 like a puzzle, thereby seating the mating surfaces 326 and 426 of the elongate cap 102 and the upper handle 402 so that they sit flush with one another. Until that occurs, when the cap 102 is completely on, the elongate cap 102 may be able to rotate slightly with respect to the handle 402. But once the mating surfaces 326 and 426 make full contact against one another, the elongate cap 102 is unable to twist or move with respect to the upper handle 402 until a disengaging force is applied. In such full contact configuration, the cut out window 434 of the lower housing 404 is aligned beneath the clear window 208 of the elongate cap 102. FIG. 6D depicts an exemplary embodiment of such positioning between the clear window 208 of the elongate cap 102 and the cut out window 434 of the lower housing 404.

During the course of aligning the elongate cap 102 along the lower housing 404, the contacting surfaces 316a-316d also help secure the elongate cap 102 to the lower housing 404. When the contacting surfaces 316a-316d engage the outer surface 418 of the lower housing 404, the friction created between contact surfaces 316a-316d and the outer surface 418 holds the elongate cap 102 against the lower housing 404. That contact prevents the elongate cap 102 from slipping and helps hold the elongate cap 102 in position until the proximal rim 210 of the elongate cap 102 and the distal rim 420 of the upper handle 402 fully engage one another. FIGS. 6E and 6F illustrate this contact with respect to the contacting surface 316a engaging the lower housing 404 while the elongate cap 102 slides against the flaring outer surface 418. As shown, as the elongate cap 102 is pushed towards the upper handle 402, larger portions of the contacting surfaces 316a and 316c make contact with the flaring outer surface 418 as shown in FIG. 6E (contact region C). As a result, the friction created between the contacting surfaces 316a-316d and the outer surface 418 increases, which provides more secure fit between the elongate cap 102 and the lower housing 404. FIG. 6F shows a transverse cross sectional view across plane B as depicted in FIG. 6E. As shown, the contacting surfaces 316a-316d near the base 314 are in full contact with the outer surface 418 of the lower housing 404. As the patient continues to slide the elongate cap 102 along the flaring outer surface 418 towards the upper handle 402, thereby closing the gap 600 shown in FIG. 6E, the patient may feel increasing resistance as the contact friction between the contacting surfaces 316a-316d and the outer surface 418 continues to increase until the proximal rim 210 and the distal rim 420 engage one another. The feel of the increasing friction, together with the alignment of the proximal 210 and distal rims 420, provide a guide for the patient to more easily reapply the cap.

Figure 7A:
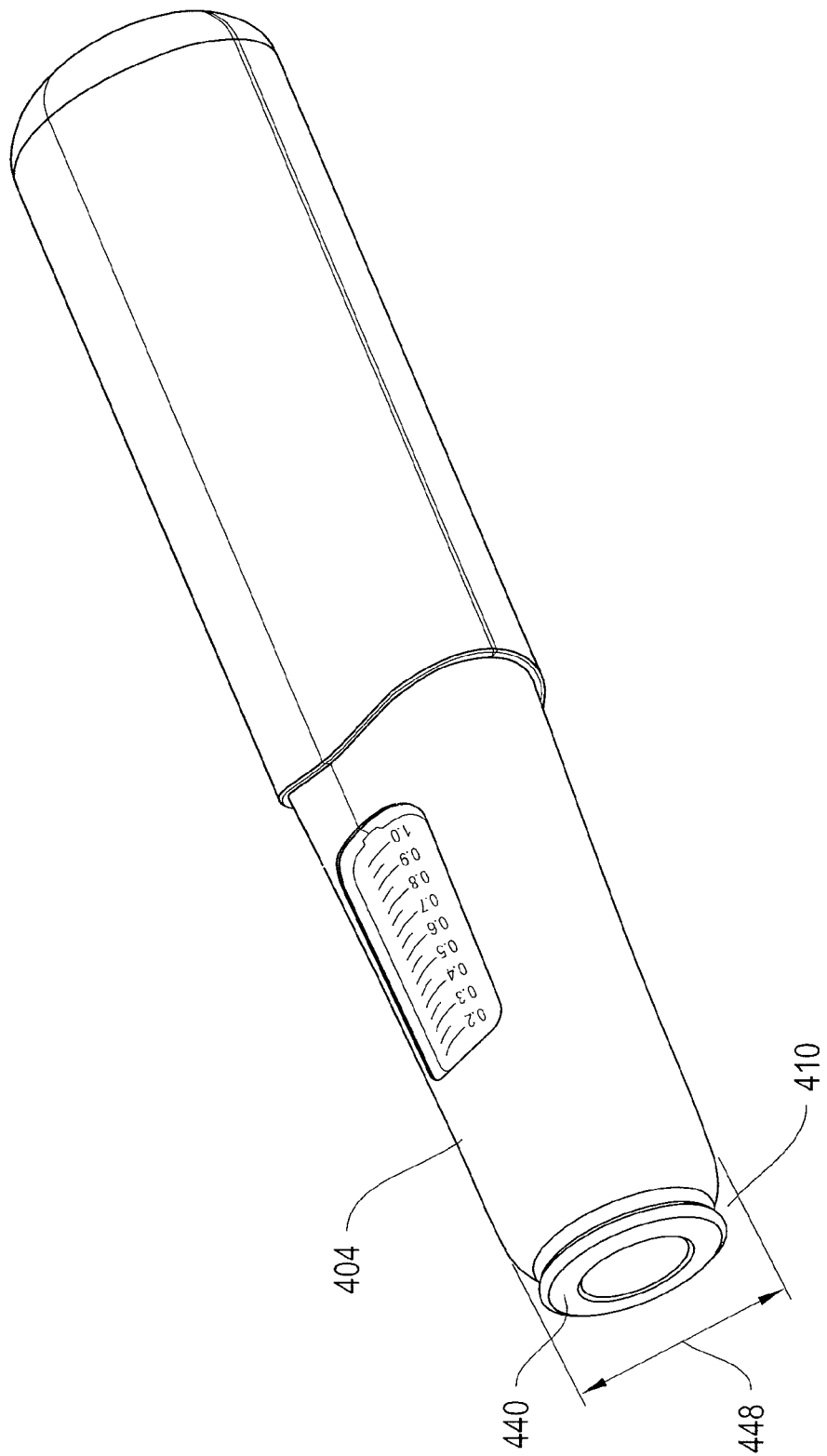
FIG. 7A depicts a perspective view of a housing according to an illustrative embodiment of the invention.
Figure 7B:
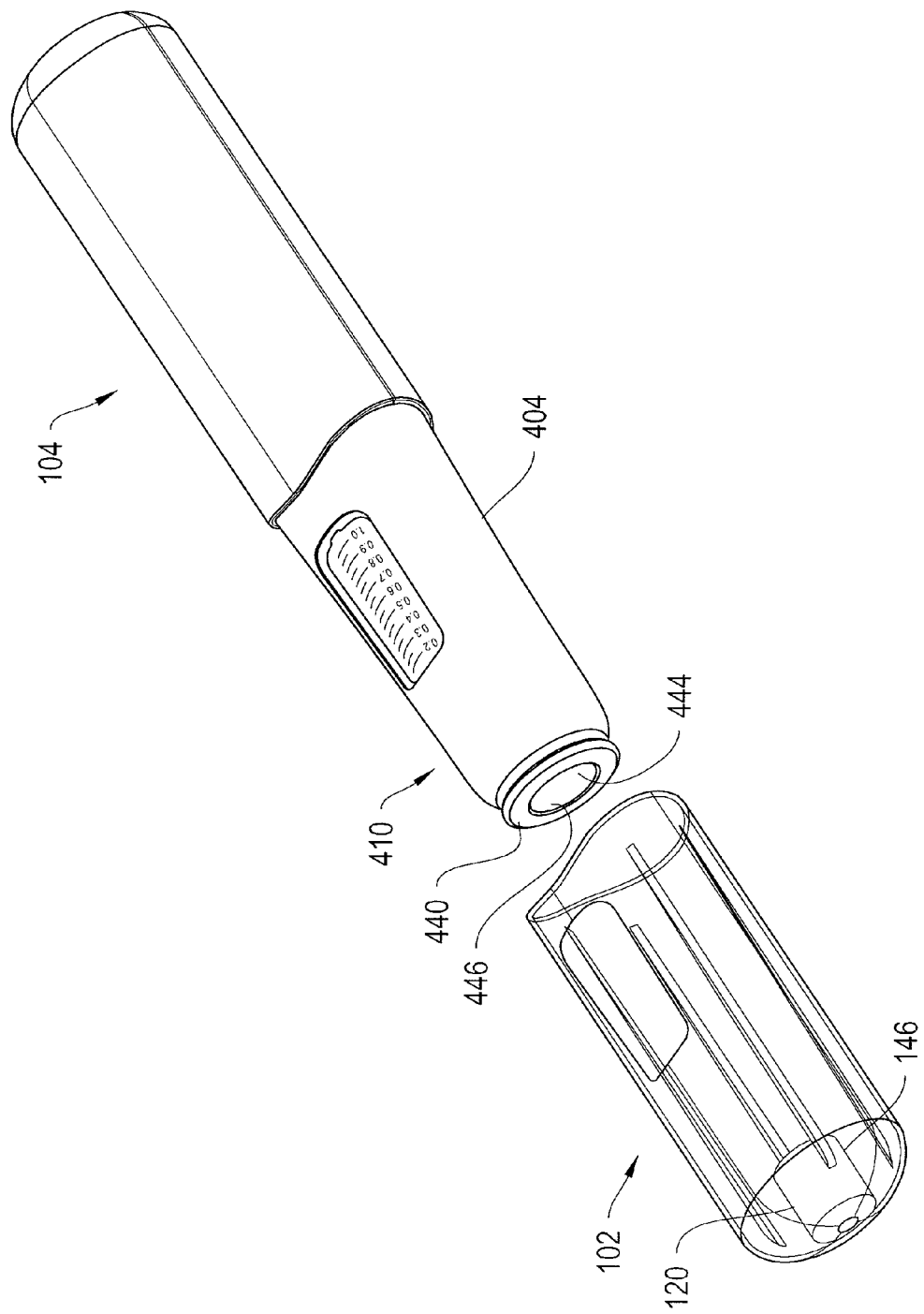
FIG. 7B shows perspective views of the housing shown in FIG. 7A and an elongate cap.

In certain embodiments, the autoinjector system of the invention also provides a more ergonomic and efficient interface between lower housing 404 and the elongate cap 102, as shown in FIGS. 7A-7B. FIG. 7A shows a perspective view of the distal end 410 of the lower housing 404. As shown, the distal end 410 of the lower housing 404 includes a large skin contacting surface 440 that contacts the patient's skin when the device is in use. The outer diameter 448 near the distal end 410 is large enough to make contact with the longitudinal ribs 310a-310d of the elongate cap 102. When the device is in use, the force applied by the autoinjector 100 spreads throughout the skin contacting surface 440, thereby more evenly distributing the force to help ease the patient comfort's level. In certain embodiments as illustrated in FIG. 7A, the skin contact surface 440 has a doughnut shape.

Figure 8:
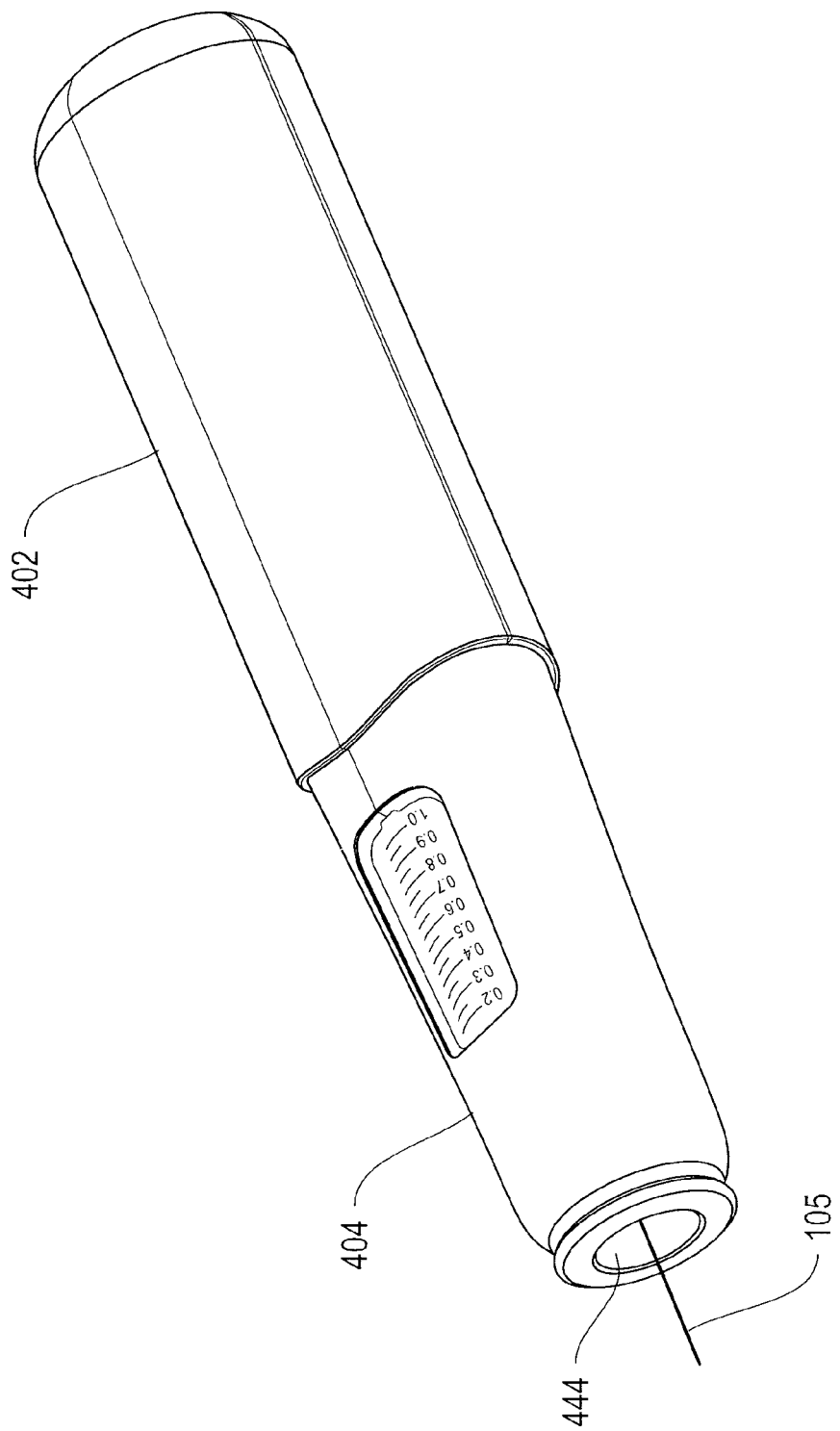
FIG. 8 shows a perspective view of an exemplary embodiment of a housing in a launch position.

As shown in FIG. 7B, the distal end 410 of the lower housing 404 is also provided with an opening, also referred to as an interfacing passage 444. When in use, the autoinjector fires and the needle 105 extends through the interfacing passage 444 to inject the medication, then retreats back through interfacing passage 444. When not in use, the interfacing passage 444 receives the connector housing pocket 120 of the elongate cap 102 to shield the patient from the needle. The connector housing pocket 120 is secured within the interfacing passage 444 as an interior receiving surface 446 of the lower housing 404 engages with a corresponding mating surface 146 of the connector housing pocket 120 in friction fit. The corresponding mating surface 146 engages with a portion of the receiving surface 446 of the lower housing 404. When the elongate cap 102 is removed from the lower housing 404, the mating surface 146 disengages from the interior receiving surface 446, which clears the interfacing passage 444 to allow the needle 105 of the syringe assembly 101 to extend through for injection. FIG. 8 shows an exemplary embodiment of the needle 105 extending through the interfacing passage 444 when the device is in a launch position. Thus, the interfacing passage 444 is sized and shaped so as to receive a portion of the elongate cap 102, when the device is in a storage position, and the syringe assembly 101 when the device is in use.

Figure 9A:
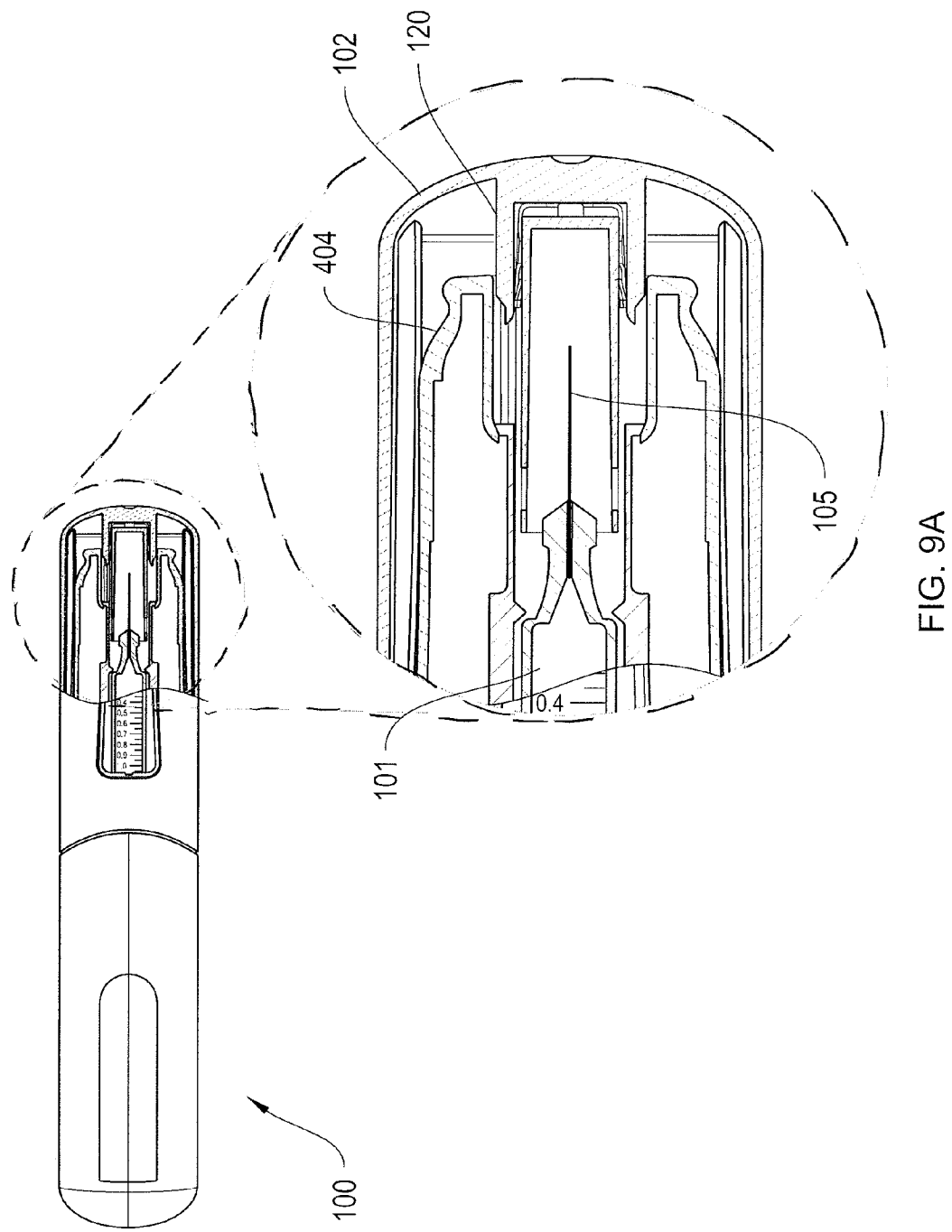
FIG. 9A depicts a cross sectional view of the elongate cap engaging a distal region of a lower housing according to an illustrative embodiment of the invention.
Figure 9B:
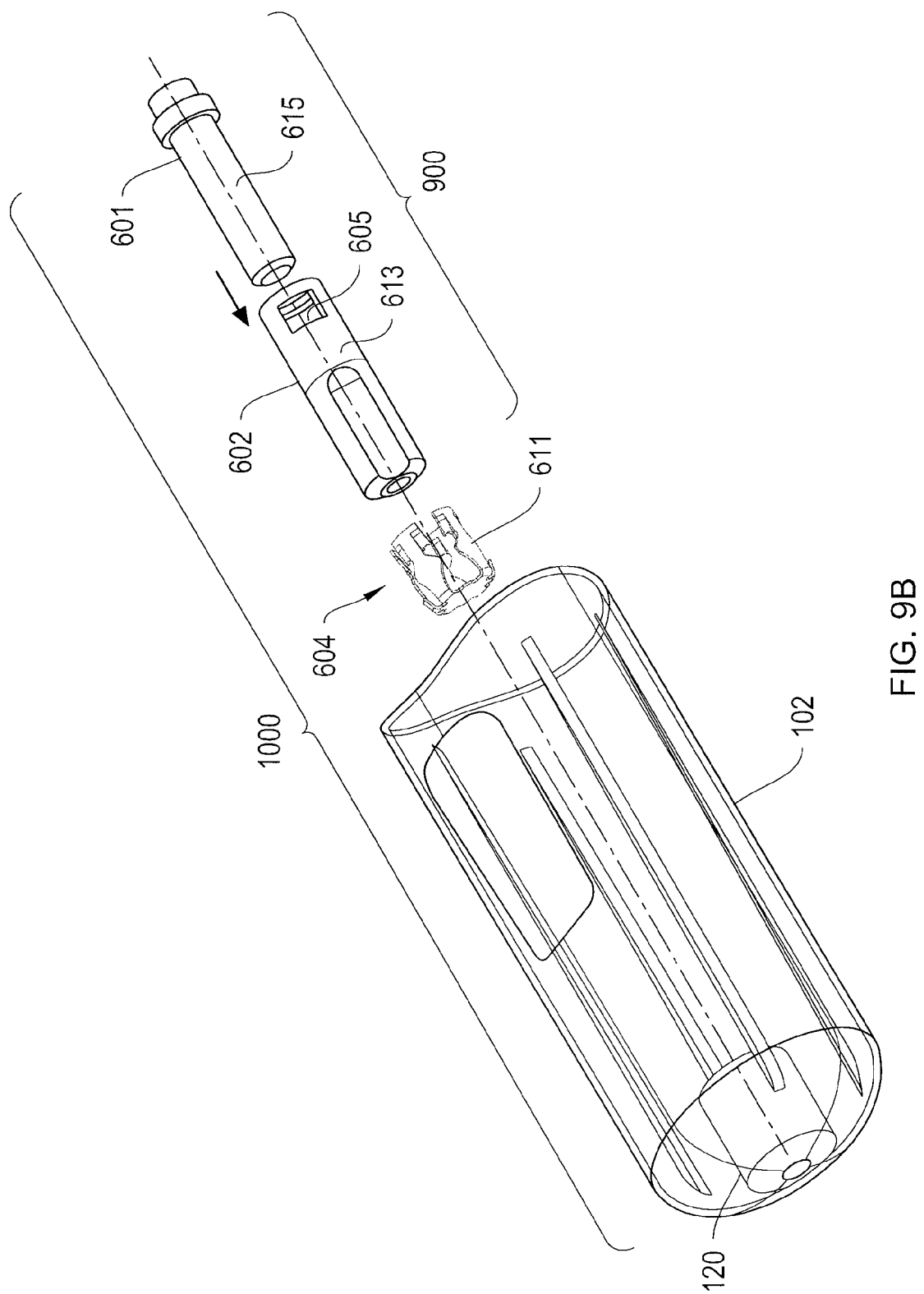
FIG. 9B depicts an exploded view of an exemplary embodiment of a needle shield and a needle shield housing being engaged to an elongate cap.

FIG. 9A depicts a cross sectional view of the elongate cap 102 being mated to the lower housing 404 when the autoinjector is in a storage position. It also shows the connector housing pocket 120 being joined to various other components that protect the needle 105 of the syringe assembly 101. These components, which form an elongate cap assembly 1000 when joined to one another, are shown in FIG. 9B. The elongate cap assembly 1000 includes a rubber needle shield 601 for shielding the needle of the syringe assembly 101, a needle shield housing 602 that grips the outer surface 615 of the rubber needle shield 601, and a connector 604 that grips the outer surface 613 of the needle shield housing 602. The connector 604 is friction fitted along its exterior surface 611 within the connector housing pocket 120 of the elongate cap 102. These components and their mating relationships are explained below.

FIGS. 10A and 10B depict perspective and cross sectional views of an exemplary embodiment of the rubber needle shield 601. As shown, the rubber needle shield 601 is cylindrical in shape and includes a shoulder 1002 near a proximal end 1001. The rubber needle shield 601 also includes a needle receiving portion 1004 that houses the needle. The needle receiving portion 1004 tapers towards a distal end 1003. The rubber needle shield 601 also includes a needle tip holding portion 1006 that extends from a tip 1005 of the needle receiving portion 1004 towards the distal end 1003. The tip holding portion 1006 houses the tip of the needle. In certain embodiments, the rubber needle shield 601 is hollow.

Figure 11A:
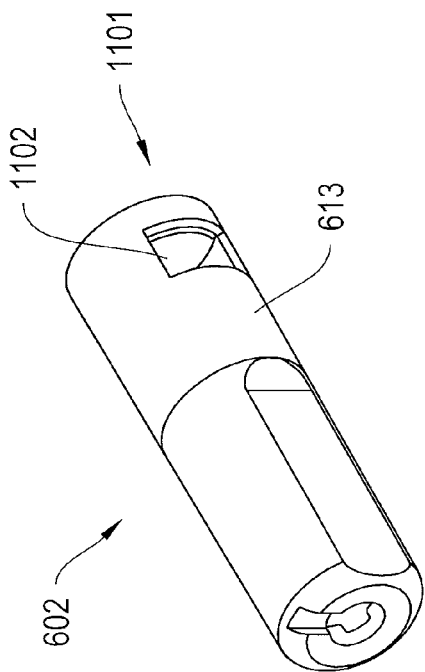
FIGS. 11A-11B depict perspective and cross sectional view of an exemplary embodiment of the needle shield housing depicted in FIG. 9B.
Figure 11B:
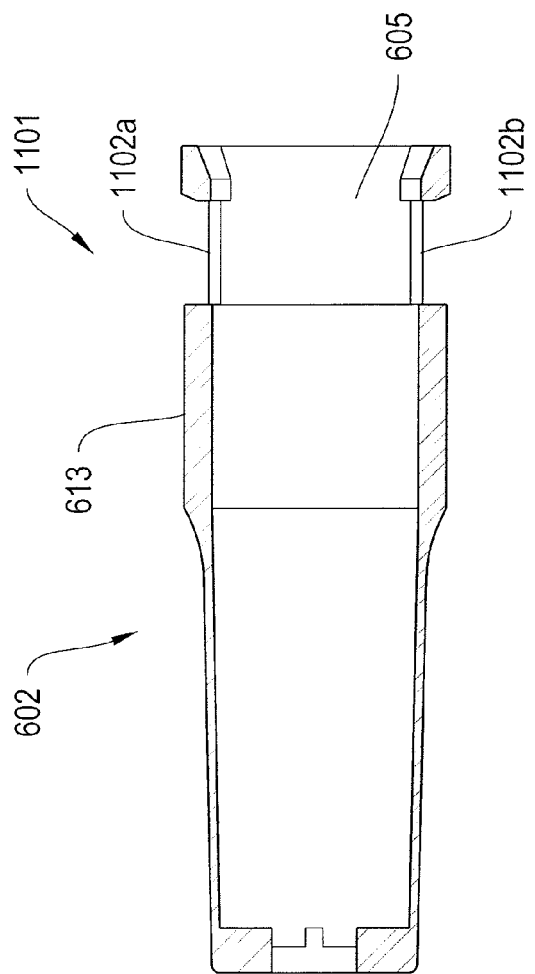
Figure 12:
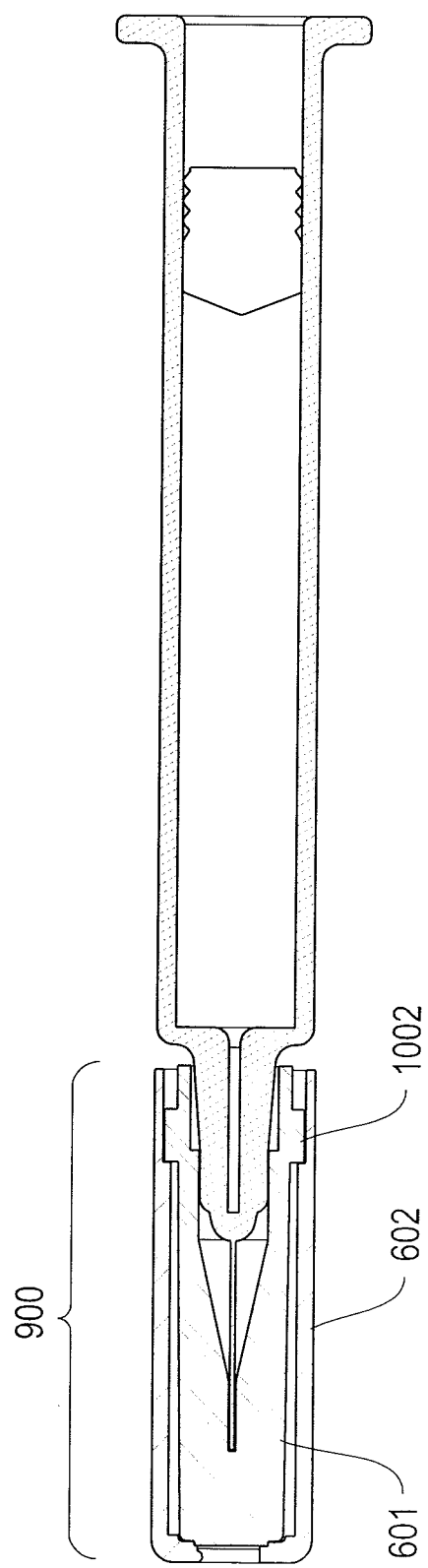
FIG. 12 shows an exemplary embodiment of the needle shield being mated to the needle shield housing.

Referring again to FIG. 9B, the rubber needle shield 601 fits within the space 605 of the needle shield housing 602. As shown in FIGS. 11A-11B, the needle shield housing 602 includes open windows 1102a and 1102b disposed on the outer surface 613 near an open end 1101. As the rubber needle shield 601 is inserted into the space 605 of the needle shield housing 602, the shoulder 1002 of the rubber needle shield 601 having the largest diameter is squeezed into the space 605 until the shoulder 1002 clicks within the open windows 1102a and 1102b. FIG. 12 illustrates an exemplary embodiment of the rubber needle shield 601 being fitted within the needle shield housing 602, forming a needle shield assembly 900. A conventional hypodermic syringe assembly (for example, a syringe assembly manufactured by Becton, Dickinson and Company) may also be used with the autoinjector described herein. The needle shield housing 602 may be made of plastic material or other material that provides structural support to the rubber needle shield 601. The needle shield assembly 900 is fitted within the connector 604, which is fitted within the elongate cap 102 as described more fully below.

Figure 13A:
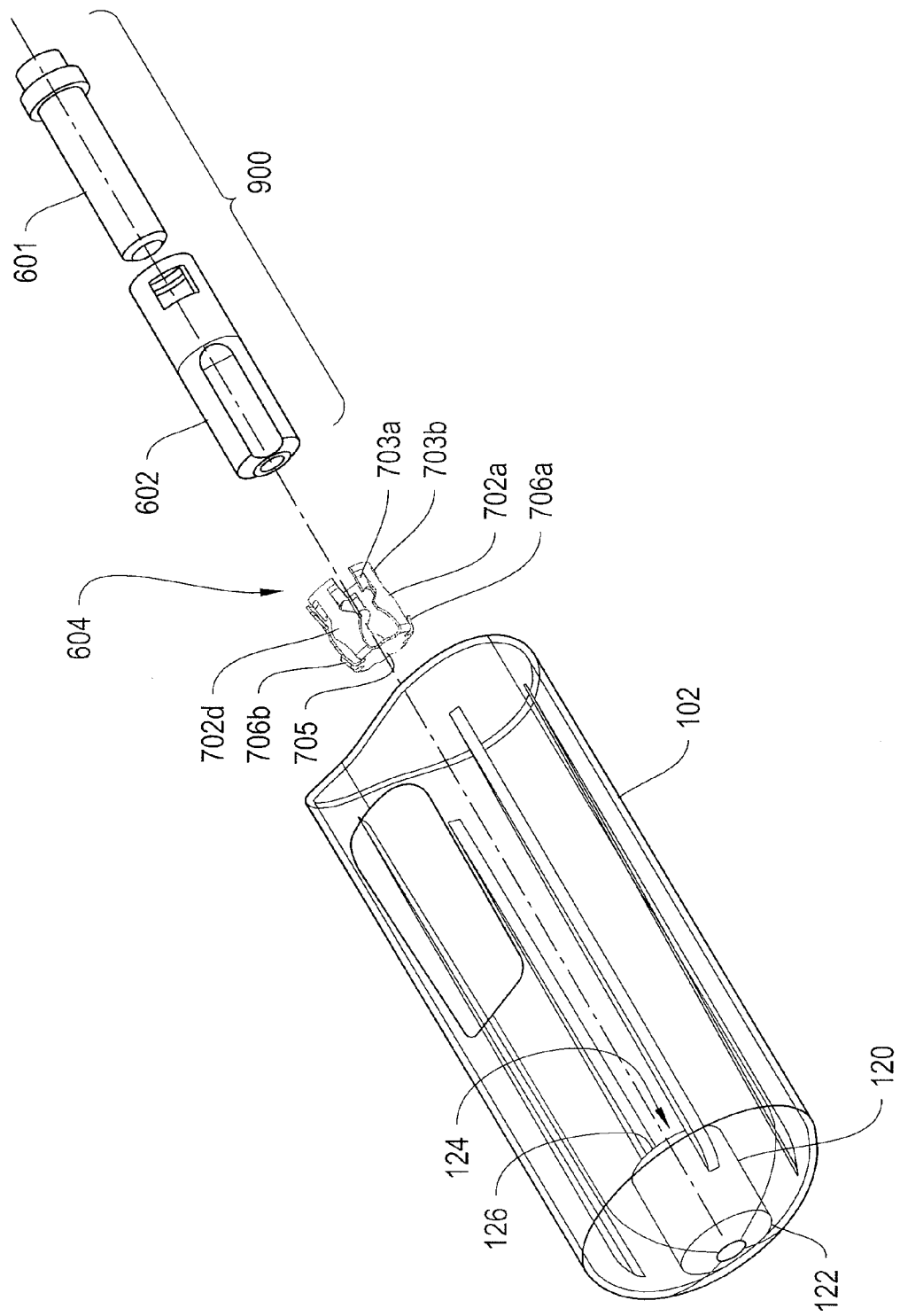
FIGS. 13A-13B show various views of the connector being inserted into the elongate cap depicted in FIG. 9B.

The connector 604 includes a number of features for securing the needle shield assembly 900 to the elongate cap 102. FIG. 13A shows an exploded view of the connector 604 being inserted within the elongate cap 102 (shown in cross sectional view for viewing clarity). As shown, the connector housing pocket 120 with a circular cross section includes a closed end surface 122 and an open end 124. The connector 604 slides within the open end 124 of connector housing pocket 120. The connector 604 includes a base 705, a plurality of first legs 702a-702d, spaced symmetrically away from one another near the proximal end 720 of the connector 604, that engage the needle shield assembly 900. The connector 604 also includes a plurality of second legs 706a-706b that extend proximally from the base 705 and having barb tips 707a-707d that flare outwardly.

Figure 13B:
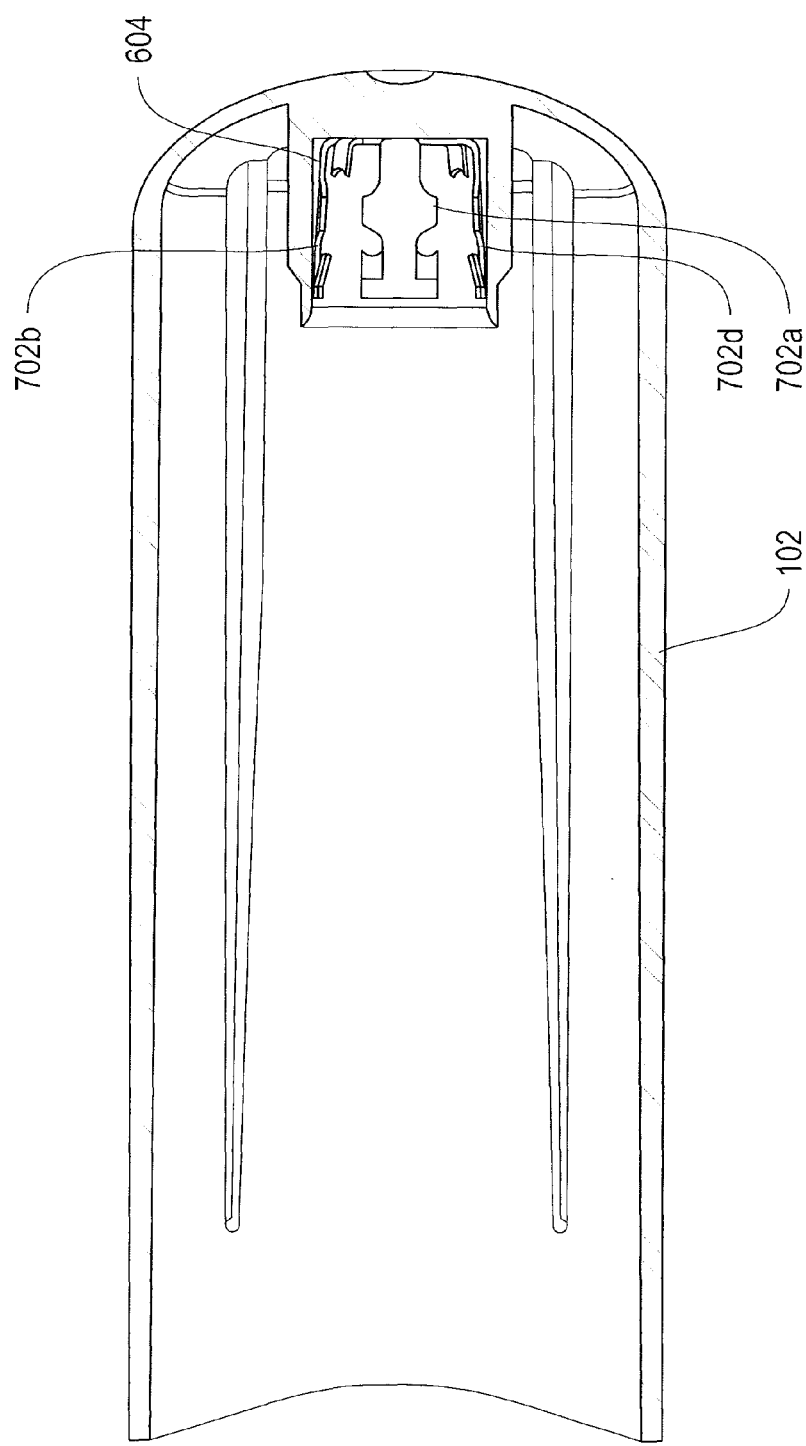
Figure 13C:
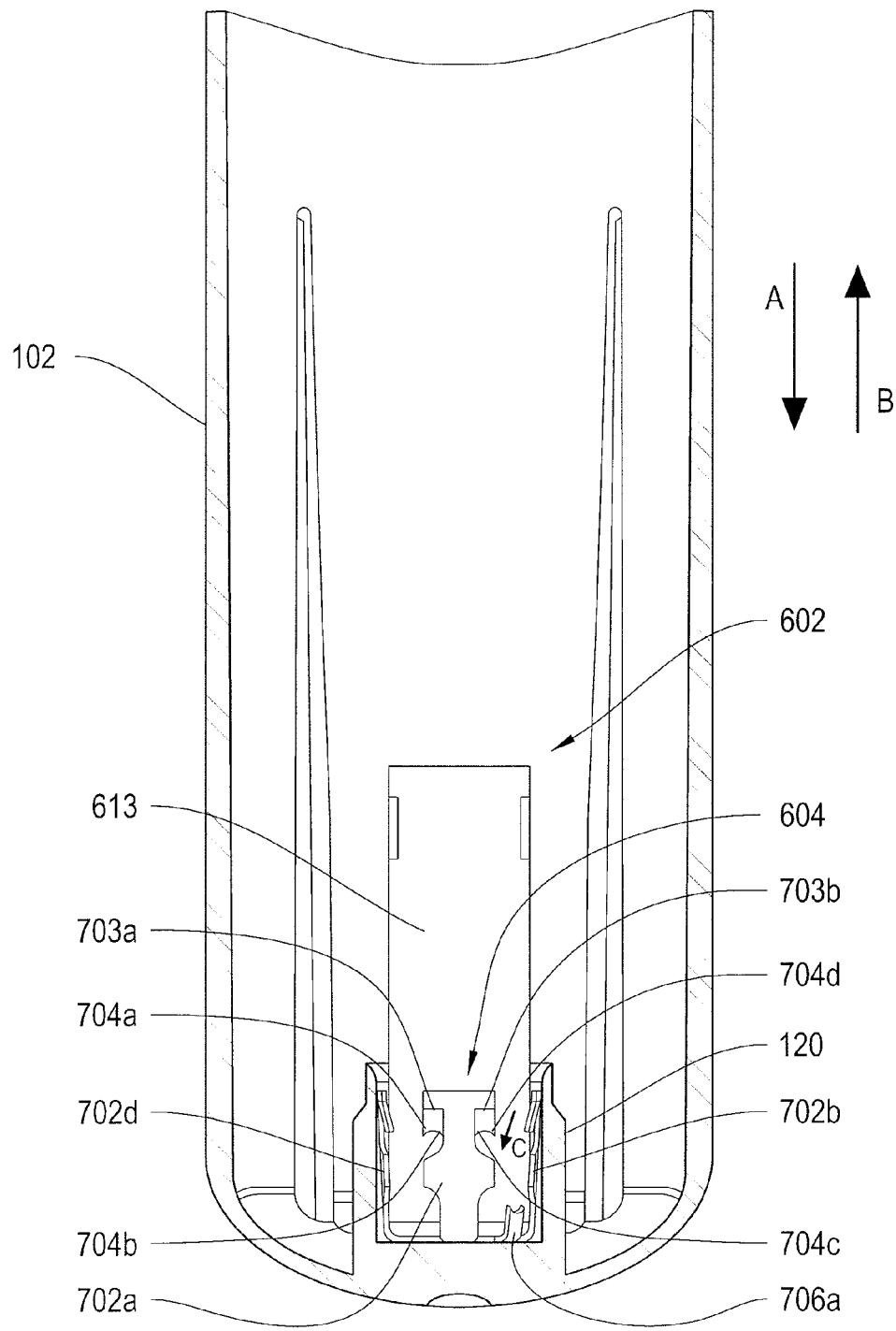
FIG. 13C depicts an exemplary mating relationship between a needle shield housing, a connector, and an elongate cap.
Figure 14A:
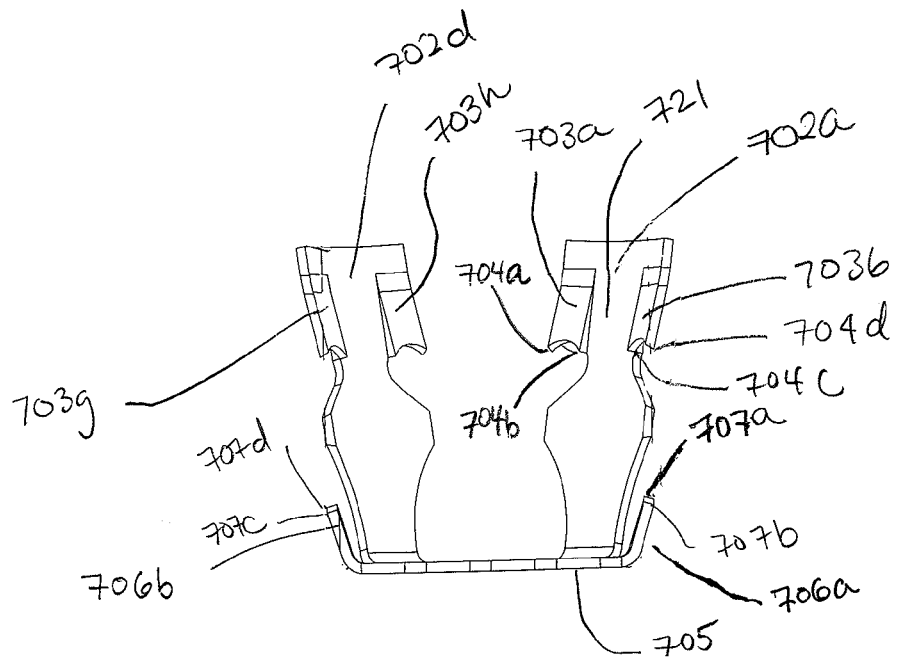
FIGS. 14A-14C depict various views of an exemplary embodiment of a connector for connecting the needle shield housing to the elongate cap as depicted in FIG. 9B.
Figure 14B:
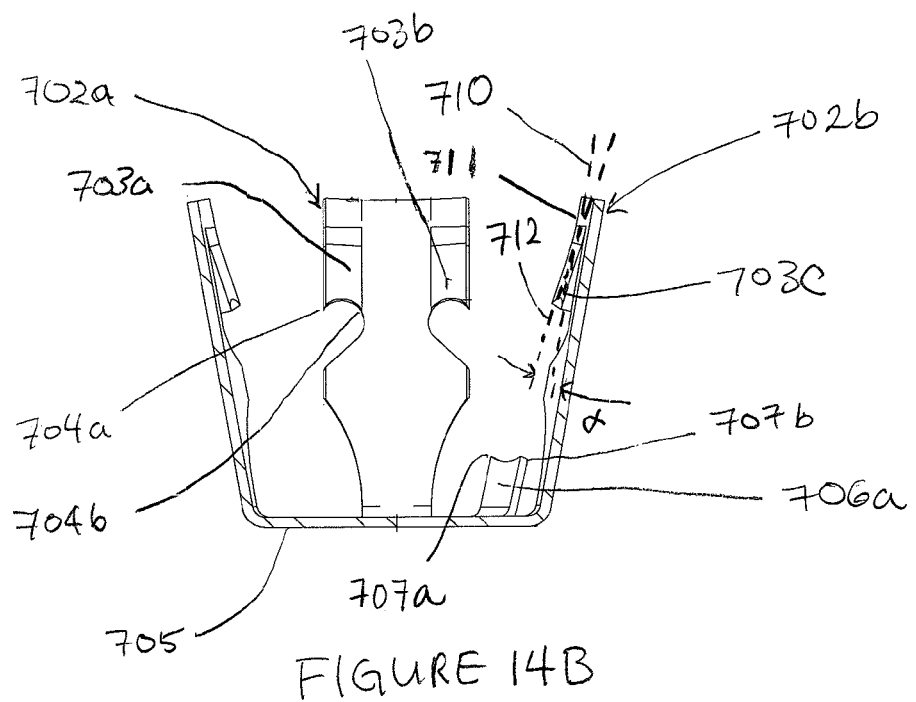
Figure 14C:
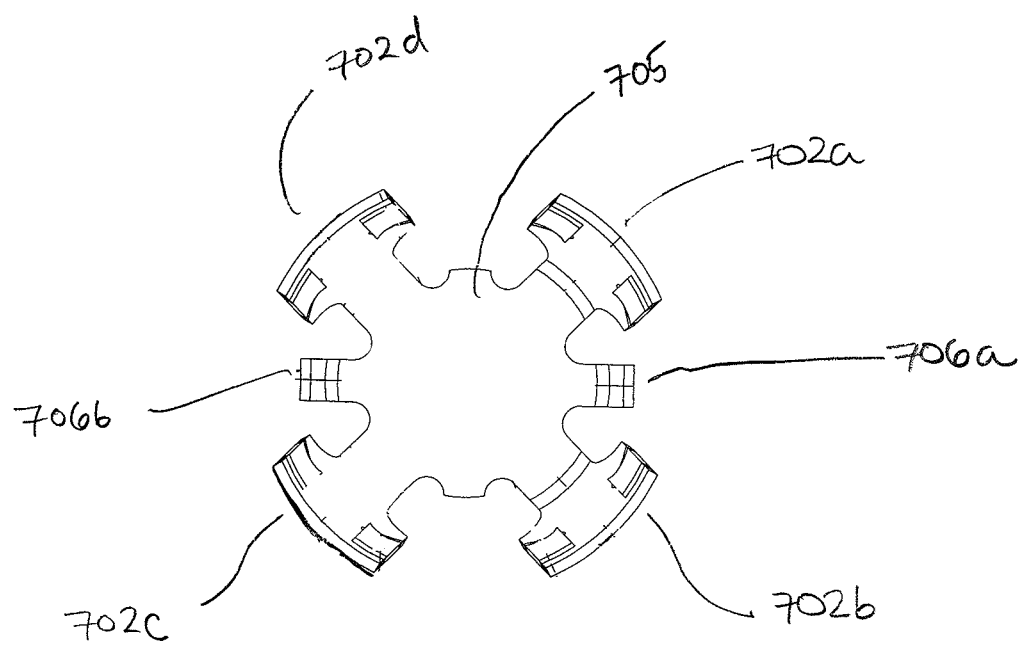

The connector 604 is initially flower shaped, as illustrated in FIG. 14A-14C, but is bent so as to be confined within a cylindrical shaped stem 126 (FIG. 13A) of the connector housing pocket 120. As a result, the plurality of first legs 702a-702d, which were initially disposed at an angle with respect to the horizontal are now about 90 degrees with respect to the horizontal (See FIGS. 13B and 13C), thereby applying an interference force (Arrow C as shown in FIG. 13C) against the outer surface 613 of the needle shield housing 602 when the needle shield 602 is received within the connector 604. More specifically, as shown in FIG. 13C, each of the first legs (e.g., 702a) includes two upper internally facing barbs (e.g., 703a-703b). The upper internally facing barbs 703 protrude inwardly and distally to receive and grip the outer surface 613 of the needle shield housing 602. FIG. 13C depicts a cross sectional view of the connector 604 engaging the outer surface 613 of the needle shield housing 602. The upper, internally facing barbs 703 are adapted to receive with minimal interference the needle shield housing 602 when the needle shield housing 602 is being inserted onto the connector 604 in the direction indicated by Arrow A. As shown, the internally facing barbs 703 are disposed at an angle such that the needle shield housing 602 slides onto the internally facing barbs 703 when it is first inserted into the connector 604. However, once engaged, upper, internally facing barbs 703, which are protruding inwardly and distally, are shaped to engage the outer surface 613 of the needle shield housing 602 and prohibit backsliding (Arrow B) of the needle shield housing 602 or removal of the connector 604 from the needle shield housing 602. As shown, the upper, internally facing barbs 703a-703h include tips 704a-704p that point toward the base 705 of the connector 604. These tips 704a-704p of the upper, internally facing barbs 703a-703h dig into the outer surface 613 of the needle shield housing 602. When the elongate cap 102 is pulled distally (Arrow A), the distally applied force causes the tips 704a-704p of the upper barbs 703a-703h to dig further into the outer surface 613 of the needle shield housing 602 as noted by Arrow C. This connection prevents the needle shield housing 602 from separating from the elongate cap 102 when a patient pulls on the elongate cap 102 distally.

As shown in FIGS. 14A-14B, the upper, internally facing barbs 703a-703h are concaved and include barb tips (e.g., 704a and 704b) that apply opposing force with respect to one another when they engage the needle shield housing 602 as the barb tips are disposed at two ends of a concaved surface (e.g., upper, internally facing barbs 703). In some embodiments, the upper, internally facing barbs 703a-703h are disposed at an angle with respect to the body of the first legs 702a-702d. This is more particularly shown in FIG. 14B. Such configuration may enhance the engagement between the needle shield housing 602 and the connector 604 as added protrusion (i.e., angled disposition of the barbs 703 with respect to the first legs 702) and allow the barb tips 704a-704p to more securely dig into the outer surface 613 of the needle shield housing 602 when the patient pulls the elongate cap 102 distally. As depicted in FIG. 14B, the longitudinal axis 710 of the upper portion 711 of the first legs 702b is disposed at angle α with respect to the center axis 712 of the upper, internally facing barb 703c. The center axis 712 may be disposed between about 3 degrees to about 30 degrees with respect to the longitudinal axis 710 of the first legs 702b. In some embodiments, as illustrated in FIG. 14A, at least one of the first legs (e.g., 702a) includes an upright 721 and a first pair of internally facing barb tips (e.g., 704a-704b) is positioned to a lateral side of the upright 721 and a second pair of internally facing barbs tips (e.g., 704c-704d) is positioned to a medial side of the upright 721. In some embodiments, the connector 604 is made by stamping a thin sheet of stainless steel and bending the first and second legs into angles with respect to the horizontal. This allows for a cost effective manufacturing and mass production.

Figure 15:
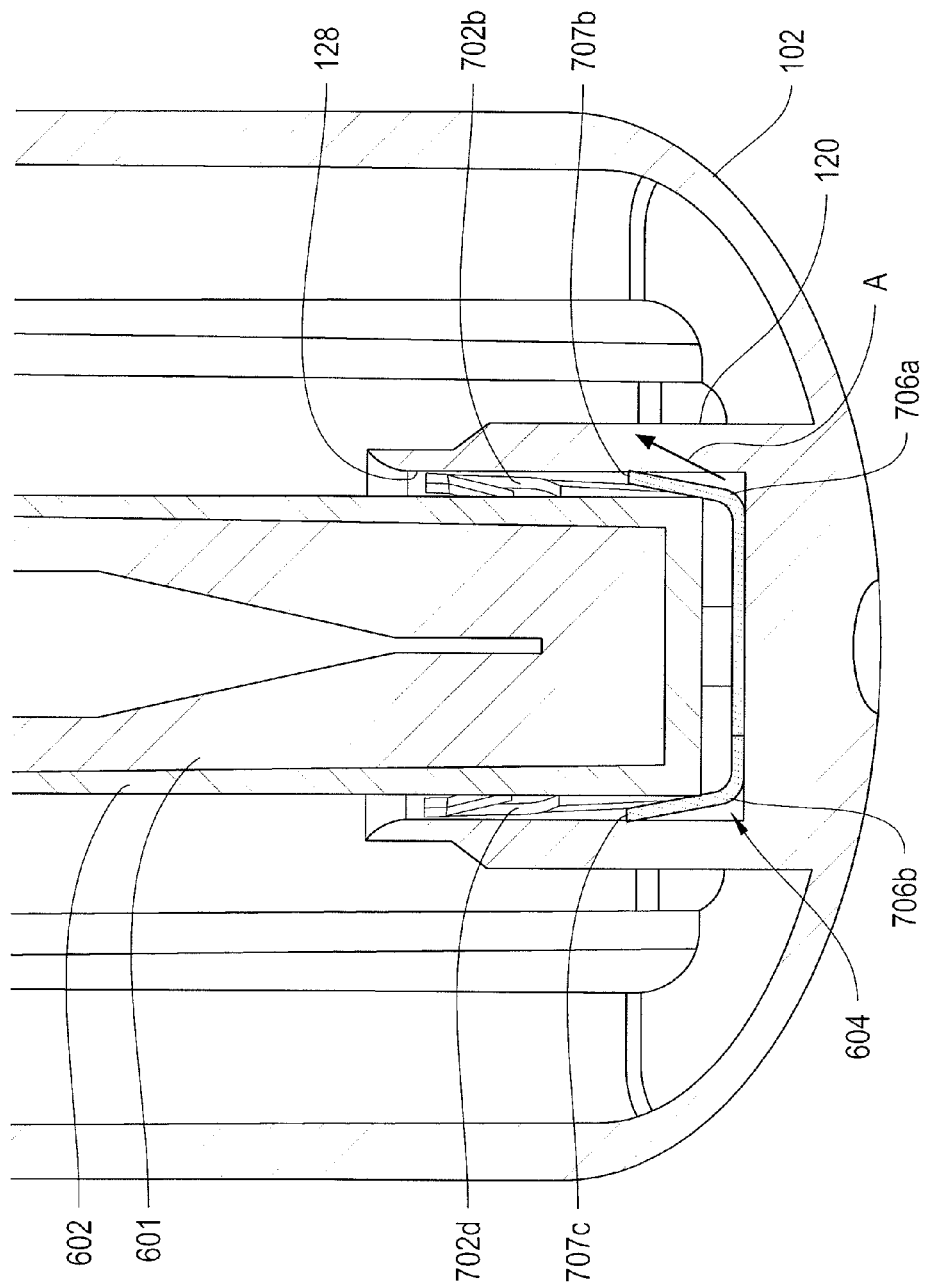
FIG. 15 depicts an exemplary mating relationship between a connector and an elongate cap.

The connector 604 also includes the plurality of second legs 706a-706b that are spaced symmetrically away from one another in the distal end of the connector 604. These second legs extend proximally from the base 705 and include lower, externally facing barb tips 707a-707d that flare outwardly toward the connector housing pocket 120 when the connector 604 is fitted within the connector housing pocket 120. As shown in FIGS. 14A-14C, a second leg (e.g., 706a) is positioned between two of the first legs (e.g., 702a and 702b). In some embodiments, the second plurality of legs 706a-706b are initially disposed more than 90 degrees (e.g., about 91 degrees to about 120 degrees) with respect to the horizontal. When the connector 604 is fitted within the connector housing pocket 120 as shown in FIG. 15, the plurality of second legs 706a-706b engage with the inner surface 128 of the connector housing pocket 120. As shown in FIG. 15, the lower, externally facing barb tips 707a-707d engage a lower, interior portion of the connector housing pocket 120, barbing the connector 604 to the elongate cap 102 in a manner similar to the connections between the upper, internally facing barb tips 704a-704p and the needle shield housing 602 as described above. As the lower, externally facing barb tips 707a-707d extend proximally into the connector housing pocket 120 (Arrow A), these barbs tips 707a-707d prevent the elongate cap 102 from disengaging from the connector 604. In some embodiments, the lower, externally facing barb tips 707a-707d dig into the inner surface 128 of the connector housing pocket 120 and remain fixed in place during use.

Figure 16:
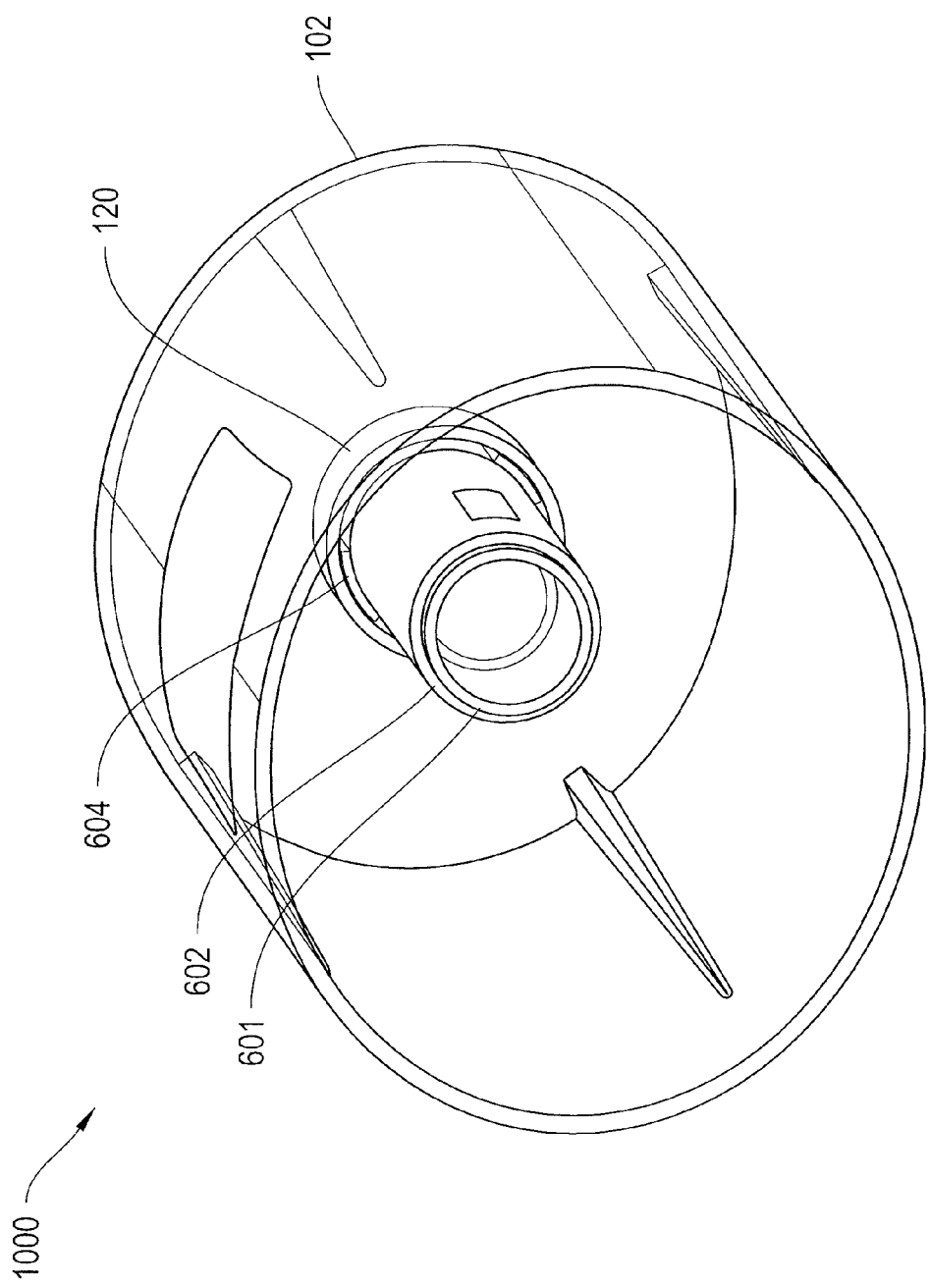
FIG. 16 depicts an exemplary mating relationship between various components of an elongate cap assembly.

FIG. 16 depicts a perspective view of the elongate cap assembly 1000, showing the rubber needle shield 601 being mated to the needle shield housing 602 (forming the needle shield assembly 900), and the connector 604 receiving the needle shield housing 602 and being fitted within the connector housing pocket 120 of the elongate cap 102. As noted above, the connector 604 fits within the connector housing pocket 120 and engages the needle shield assembly 900, connecting permanently to the needle shield assembly 900 by the expanding force of the bent flower legs, such that the barbs engage and, if the elongate cap 102 is pulled distally by the patient, the entire elongate cap assembly 1000 (including the rubber needle shield 601 covering the needle) is removed as a unit. In some embodiments the needle shield housing 602 is asymmetrical in shape, which allows at least one pair of legs (e.g., 702a and 702c) of the connector 604 to make contact with the outer surface 613 of the needle shield housing 602 such that when the elongate cap 102 is pulled, the elongate cap assembly 1000 is removed as a unit. In some embodiments, only one but not both pairs of legs connect with the needle shield housing 602.

In certain implementations, the autoinjector system 100 is provided to the patient in a kit including the autoinjector system and an alcohol swab. In certain embodiments the autoinjector system 100 is pre-filled with medication. In certain embodiments, the system 100 is packaged with a pre-filled syringe that is inserted within the system 100 prior to commercial sale. The pre-filled syringe includes medication to be used to treat RA. Particular examples of medication include viscous medications containing proteins or peptides especially antibodies or fragments thereof, including pegylated antibody fragments. The systems and methods may in particular be used to administer the pegylated antibody fragment known as certolizumab pegol. The medication may be for treatment of any disease or disorder, including for the treatment of rheumatoid arthritis. In certain embodiments, the viscosity of the liquid medication is less than about 120 mPa·s (120 centipoise), preferably less than 100 mPa·s (100 centipoise) at a delivery temperature of 20° C. In certain embodiments, the viscosity of the liquid medication is between about 65 centipoise and about 120 centipoise. In certain embodiments, the viscosity of the liquid medication is between about 75 centipoise and about 100 centipoise. In certain embodiments, the viscosity of the liquid medication is higher than about 65 mPa·s, preferably higher than 85 mPa·s. In certain embodiments the viscosity of the liquid medication is about 80 centipoise. In certain embodiments, the liquid medication is designed for refrigerated rest (e.g. at from 2-8° C.) and for injected delivery at room temperature (e.g. at or about 18-30° C.). It is to be understood that while the invention has been described in conjunction with the various illustrative embodiments, the forgoing description is intended to illustrate and not limit the scope of the invention. For example, a variety of systems and/or methods may be implemented based on the disclosure and still fall within the scope of the invention. For example, the elongate cap described herein may be used with devices described in, for example, WO2005/070481, or other equivalent pen needles or autoinjectors for automatically injecting drugs to patients. Other aspects, advantages, and modifications are within the scope of the following claims. All references cited herein are incorporated by reference in their entirety and made part of this application.

The invention claimed is:

1. An autoinjector device comprising:
 a housing;
 a syringe assembly slidably mounted on the housing, the syringe assembly including a needle and a fluid container;
 an auto injector actuator for urging the syringe assembly with respect to the housing from a storage position to a launch position;
 a needle cap remover; and
 a cap releasably engaged to the housing, the cap having a protruding pocket for receiving the needle cap remover;
 the needle cap remover comprising a connector having:

a base;
    a plurality of first legs spaced symmetrically away from one another and extending proximally from the base, each first leg having an internally facing barb for receiving and engaging a needle cap that covers the needle of the syringe assembly; and
    a plurality of second legs extending proximally from the base, each second leg having an externally facing barb tip that flares outwardly towards the protruding pocket for engaging a lower, interior portion of the protruding pocket near the base, wherein at least one of the second legs is positioned circumferentially between two of the first legs, and wherein the plurality of second legs do not extend proximally from the base as far as the plurality of first legs.

2. The device of claim 1, wherein the internally facing barbs include a tip that flares inward and towards the base.

3. The device of claim 2, wherein the tip of at least one of the first legs dig into the needle cap.

4. The device of claim 1, wherein the internally facing barbs are concaved.

5. The device of claim 1, wherein at least one of the first legs includes an upright and a first pair of internally facing barb tips positioned to a lateral side of the upright and a second pair of internally facing barb tips positioned to a medial side of the upright.

6. The device of claim 5, wherein the internally facing barbs extend at an angle with respect to the upright.

7. A device comprising:
a needle cap remover;
a housing having distal and proximal ends, the distal end having an interfacing passage that receives a cap; wherein the cap releasably engages the housing and has a protruding pocket for receiving the needle cap remover;
a syringe assembly including a needle and a fluid container; and
the needle cap remover comprising a connector having:
    a base;
    a plurality of first legs spaced symmetrically away from one another and extending proximally from the base, each first leg having an internally facing barb for receiving and engaging a needle cap that covers the needle of the syringe assembly; and
    a plurality of second legs extending proximally from the base, each second leg having an externally facing barb tip that flares outwardly towards the protruding pocket for engaging a lower, interior portion of the protruding pocket near the base, wherein at least one of the second legs is positioned circumferentially between two of the first legs, and wherein the plurality of second legs do not extend proximally from the base as far as the plurality first legs.

8. The device of claim 7, wherein the cap covers about half of the length of the device.

9. The device of claim 8, wherein the housing includes a corresponding window positioned beneath the clear window of the cap when the cap is engaged to the housing.

10. The device of claim 7, wherein the cap includes a clear window disposed between a closed end and an open end.

11. The device of claim 7, wherein the cap includes longitudinal ribs extending along the length of the cap.

12. The device of claim 11, wherein the longitudinal ribs extend within the cap.

13. The device of claim 11, wherein the longitudinal ribs are spaced apart so that at least one rib extends on one side of a clear window and at least one rib extends on opposite side of the clear window.

14. The device of claim 11, wherein the cap includes a curved interface and the housing includes a corresponding curved interface adapted to mate with the curved interface of the cap.

\* \* \* \* \*